(12) United States Patent
Sun et al.

(10) Patent No.: US 11,479,588 B2
(45) Date of Patent: Oct. 25, 2022

(54) CATHELICIDIN-EXPRESSING LACTIC ACID BACTERIA

(71) Applicant: Jiangnan University, Wuxi (CN)

(72) Inventors: Jia Sun, Wuxi (CN); Li-Long Pan, Wuxi (CN); Diana Julien, Wuxi (CN); Ming Zhang, Wuxi (CN); Wei Chen, Wuxi (CN); Hao Zhang, Wuxi (CN)

(73) Assignee: Jiangnan University, Wuxi (CN)

( * ) Notice: Subject to any disclaimer, the term of this patent is extended or adjusted under 35 U.S.C. 154(b) by 0 days.

(21) Appl. No.: 17/529,396

(22) Filed: Nov. 18, 2021

(65) Prior Publication Data
US 2022/0064239 A1    Mar. 3, 2022

Related U.S. Application Data

(63) Continuation of application No. PCT/CN2021/083282, filed on Mar. 26, 2021.

(30) Foreign Application Priority Data

Mar. 27, 2020  (CN) .......................... 2020102292989
Mar. 27, 2020  (CN) .......................... 2020102306568

(51) Int. Cl.
| | | |
|---|---|---|
| *A61K 35/747* | (2015.01) | |
| *A61K 35/00* | (2006.01) | |
| *C07K 14/47* | (2006.01) | |
| *A23L 33/135* | (2016.01) | |
| *A61P 1/00* | (2006.01) | |
| *A61K 39/00* | (2006.01) | |

(52) U.S. Cl.
CPC ........ *C07K 14/4723* (2013.01); *A23L 33/135* (2016.08); *A61K 35/747* (2013.01); *A61K 39/0005* (2013.01); *A61P 1/00* (2018.01); *A23V 2002/00* (2013.01); *A23Y 2220/49* (2013.01); *A23Y 2220/67* (2013.01); *A61K 2035/115* (2013.01)

(58) Field of Classification Search
None
See application file for complete search history.

(56) References Cited

U.S. PATENT DOCUMENTS

| | | | |
|---|---|---|---|
| 2006/0292551 A1 | 12/2006 | Gallo et al. | |
| 2010/0310514 A1* | 12/2010 | Cho | ............... A61K 48/0008 536/23.7 |
| 2021/0380994 A1* | 12/2021 | Willcoxon | ............ A61P 39/00 |

FOREIGN PATENT DOCUMENTS

| | | |
|---|---|---|
| CN | 1878789 A | 12/2006 |
| CN | 105816854 A | 8/2016 |
| CN | 111333713 A | 6/2020 |
| CN | 111411054 A | 7/2020 |

OTHER PUBLICATIONS

Zhang et al. Zhang et al. J. Immunol. 196: 1799-1809, 2016.*
Zhang et al. Gene Therapy 20: 751-760, 2013.*
Wouters et al. Appl. Environ. Microbiol. 67: 5171-5178, 2001.*
Yin et al. J. Food Sci. Biotechnol. 39(8): 17-25, 2020.*

* cited by examiner

*Primary Examiner* — S. Devi
(74) *Attorney, Agent, or Firm* — IPro, PLLC; Na Xu

(57) ABSTRACT

The disclosure discloses cathelicidin-expressing lactic acid bacteria, and belongs to the technical field of genetic engineering. The disclosure constructs *Lactococcus. lactis* and *Lactobacillus. plantarum* expressing a CRAMP protein by optimizing the nucleotide sequence of the CRAMP protein. The *Lactobacillus* constructed in the disclosure can be used to prepare a vaccine for regulation of intestinal flora disorder, and has advantages in regulation of intestinal flora and intestinal immune response and maintenance. An anaculture can be directly taken as an oral vaccine to stimulate mice and cause a strong cellular immune response. The recombinant *L. lactis* can be used as a new oral vaccine product with good industrial prospects, plays a positive role in reducing intestinal inflammation, and has important practical significance for promoting health development of the intestinal tract.

12 Claims, 29 Drawing Sheets

Specification includes a Sequence Listing.

CATHELICIDIN-EXPRESSING LACTIC ACID BACTERIA

The instant application contains a Sequence Listing in ASCII format as a file named seq.txt, created on Aug. 11, 2022, of 4 kB in size, which is hereby incorporated by reference in its entirety.

TECHNICAL FIELD

The disclosure relates to cathelicidin-expressing lactic acid bacteria, and belongs to the technical field of genetic engineering.

BACKGROUND

Antimicrobial peptides are the main components of the innate immunity and defense of many hosts such as plants, invertebrates and vertebrates (including humans). Cathelicidins are a major class of antimicrobial peptides, and are characterized by a conservative N-terminal precursor sequence called cathelin. The conservation of the cathelin sequence indicates that various members of this family evolved from duplication and modification of common ancestor genes. The CRAMP (Cathehcidin-Related AntiMicrobial Peptide) contains 34 amino acids (GLLRKGGEKIGEKLKKIGQKIKNFFQKLVPQPEQ, SEQ ID NO: 2) and has strong antimicrobial activities against gram-positive and gram-negative bacteria, but has no hemolytic activity on human red blood cells. CRAMP at 1 mM can directly cause immediate permeabilization of the inner membrane of *E. coli*. Antibodies against CRAMP shows abundant CRAMP expression in bone marrow progenitors and neutrophils. In addition, studies have found that CRAMP has strong antimicrobial activities against some pathogenic fungi (Candia alicans and *Aspergillus fumigatus*). In vitro studies have confirmed that CRAMP can significantly inhibit proliferation of *Helicobacter pylori*. The lack of CRAMP can lead to aggravation of colitis in mice, while treatment of CRAMP knockout mice with colitis by CRAMP-expressing *Lactobacillus* has a significant alleviation effect.

CRAMP level in the intestinal tract is significantly decreased due to destruction of the intestinal barrier, resulting in the inability to exert an immune-modulatory effect and regulate the balance of intestinal flora. Therefore, choosing a safe and non-toxic carrier system that can survive in the intestinal tract and express CRAMP, so that CRAMP can play a role in the intestinal tract, is of great significance for regulating the balance of intestinal flora.

Due to high adhesion of surface molecules, *Lactococcus. lactis* and *Lactobacillus. plantarum* can successfully colonize the intestinal tract of animal bodies and become the dominant flora in the intestinal tract to play a variety of functions such as improving the body's immunity, promoting absorption of nutrients, and maintaining the balance of the intestinal flora. The formed biologically stable barrier is an important guarantee for maintaining the balance of intestinal microbes. In terms of expressing foreign genes, a *L. lactis* expression system and a *L. plantarum* expression system as prokaryotic expression systems have the following advantages: (1) as food-grade bacteria, the expression systems are safer as live carrier vaccines; (2) a foreign gene can be expressed in the cell, and can also be expressed and displayed on the cell surface or secreted out of the cell; (3) the expression systems are safe and free of endotoxin, have no need to purify and express foreign protein, and can be taken directly with the bacteria; and (4) the expression systems can colonize on the surface of a body's mucosa (belonging to a common mucosal immune system), and inoculation to a certain site on the mucosa can induce a systemic mucosal immune response; last but not least, this kind of immunity can help the body gain longer-term immunological memory, so as to resist the invasion of pathogens for a long time.

SUMMARY

The disclosure aims at solving the technical problem of overcoming the shortcomings of the prior art that oral CRAMP is easily degraded by digestive tract enzymes, and intestinal targeted delivery of CRAMP and maximization of a local immunoregulatory effect cannot be achieved, and provides a recombinant *Lactobacillus* that secretes and expresses CRAMP protein and an application thereof.

The disclosure provides a gene encoding CRAMP protein, and the gene includes a nucleotide sequence as shown in SEQ ID NO: 1.

In an embodiment, the gene is also fused with a nucleotide sequence encoding a Usp45 signal peptide, the nucleotide sequence encoding the Usp45 signal peptide is shown in SEQ ID NO: 3, and a gene sequence linked to the signal peptide is shown in SEQ ID NO: 4.

In an embodiment, a linker sequence is between the nucleotide sequence encoding the Usp45 signal peptide and the gene sequence of the CRAMP protein, and the nucleotide sequence is shown in SEQ ID NO: 10.

The disclosure further provides a vector carrying the gene.

In an embodiment, the vector is pMG36e or pNZ8148.

In an embodiment, the vector is pMG36e-CRAMP, pNZ8148-CRAMP, pNZ8148-Usp45-CRAMP, pMG36e-Usp45-CRAMP, pMG36e-Usp45-Linker-CRAMP or pNZ8148-Usp45-Linker-CRAMP.

The disclosure further provides a *Lactobacillus* expressing the CRAMP protein and the gene as shown in SEQ ID NO. 1, or the CRAMP protein which is (a) or (b):

(a) a CRAMP protein as shown in SEQ ID NO. 2; and (b) a protein derived from (a), with one or several amino acids deleted, substituted, or increase and decrease on the basis of (a), and has antimicrobial properties.

In an embodiment, the *Lactobacillus* is *L. plantarum* or *L. lactis*.

In an embodiment, *L. plantarum* FCQHC24L1 is used as a host.

In an embodiment, the *L. plantarum* FCQHC24L1 was disclosed in a 2019 paper entitled "Study on the Differences in the Genome and Main Physiological Characteristics of *L. plantarum* in Different Ecological Niches". The applicant promises to distribute the strain to the public who implement the disclosure through legal channels within 20 years from the date of application.

In an embodiment, the *L. plantarum* expresses the CRAMP protein-encoding gene with pMG36e or pNZ8148 as a vector.

In an embodiment, a Usp45 signal peptide is also introduced into the *L. plantarum* to promote expression of the CRAMP protein.

In an embodiment, the Usp45 is linked to the CRAMP gene through a linker, and the linker includes 2 or more amino acid residues selected from Gly and Ser.

In an embodiment, the amino acid sequence of the linker is GGGGS (SEQ ID NO: 13), and the nucleotide sequence encoding the linker is shown in SEQ ID NO. 9.

In an embodiment, L. lactis NZ9000 is used as a host.

In an embodiment, the L. lactis uses pMG36e or pNZ8148 as a vector.

In an embodiment, the Usp45 signal peptide is also introduced into the L. lactis to promote expression of the CRAMP protein.

The disclosure further provides a method for constructing the CRAMP-encoding L. plantarum, including: linking the CRAMP protein-encoding gene as shown in SEQ ID NO. 1 to a vector, and then transforming the gene into a L. plantarum cell; and the vector is pMG36e or pNZ8148.

In an embodiment, a Usp45 signal peptide is linked to the pMG36e or pNZ8148.

In an embodiment, the Usp45 is linked to the CRAMP gene through a linker, and the nucleotide sequence of the linker is GGCGGTGGCGGCAGC (SEQ ID NO:9).

In an embodiment, the method includes the following steps:
(1) synthesizing the CRAMP protein-encoding gene as shown in SEQ ID NO.1; and
(2) linking the gene synthesized in step (1) to pMG36e to obtain a recombinant plasmid pMG36e-CRAMP; and transforming the pMG36e-CRAMP recombinant plasmid into L. plantarum FCQHC24L1 by an electrotransformation method to obtain recombinant L. plantarum FCQHC24L1/pMG36e-CRAMP.

In an embodiment, the method includes the following steps:
(1) synthesizing the CRAMP protein-encoding gene as shown in SEQ ID NO.10; and
(2) linking the gene synthesized in step (1) to pMG36e to obtain a recombinant plasmid pMG36e-Usp45-Linker-CRAMP; and transforming the pMG36e-Usp45-Linker-CRAMP recombinant plasmid into L. plantarum FCQHC24L1 by an electrotransformation method to obtain recombinant L. plantarum FCQHC24L1/pMG36e-Usp45-Linker-CRAMP.

In an embodiment, specific operations of the electrotransformation method include: preparing competent cells of L. plantarum FCQHC24L1, transforming the recombinant plasmid, mixing and transferring the cells to an electroporation cuvette, adding a recovery MRS medium after electric shock, and culturing the cells in a static state after treatment in an ice bath, and screening high-copy transformants on a plate.

The disclosure further provides a method for constructing any one of the mentioned above recombinant L. lactis, including: linking the CRAMP protein-encoding gene as shown in SEQ ID NO. 1 to a vector, and then transforming the gene into a L. lactis cell; and the vector is pMG36e or pNZ8148.

In an embodiment, a Usp45 signal peptide is linked to the pMG36e or pNZ8148.

In an embodiment, the method includes the following steps:
(1) synthesizing the CRAMP protein-encoding gene as shown in SEQ ID NO.1; and
(2) linking the gene synthesized in step (1) to pMG36e to obtain a recombinant plasmid pMG36e-Usp45-CRAMP; and transforming the pMG36e-Usp45-CRAMP recombinant plasmid into L. lactis NZ9000 by an electrotransformation method to obtain recombinant L. lactis NZ9000/pMG36e-Usp45-CRAMP.

In an embodiment, the method includes the following steps:
(1) synthesizing the CRAMP protein-encoding gene as shown in SEQ ID NO. 4; and
(2) linking the gene synthesized in step (1) to pNZ8148 to obtain a recombinant plasmid pNZ8148-Usp45-CRAMP; and transforming the pNZ8148-Usp45-CRAMP recombinant plasmid into L. lactis NZ9000 by an electrotransformation method to obtain recombinant L. lactis NZ9000/pNZ8148-Usp45-CRAMP.

In an embodiment, the electrotransformation method includes: preparing competent cells of L. lactis NZ9000, transforming the recombinant plasmid, mixing and transferring the cells to an electroporation cuvette, adding a recovery MRS medium after electric shock, and culturing the cells in a static state after treatment in an ice bath, and screening high-copy transformants on a plate.

The disclosure further provides an edible or medicinal composition, and the composition contains the L. lactis and/or L. plantarum.

In an embodiment, the concentration of L. lactis and/or L. plantarum in the composition is greater than or equal to $1 \times 10^5$ CFU/mL or $1 \times 10^5$ CFU/g.

In an embodiment, the composition is a medicine and contains a pharmaceutically acceptable carrier.

The disclosure further provides an application of the L. lactis and/or L. plantarum in preparing a vaccine.

In an embodiment, the vaccine is an oral vaccine for preventing acute colitis.

In an embodiment, the application is to culture the L. lactis, and then use the anaculture of L. lactis as an oral vaccine.

In an embodiment, the application includes the following steps: inoculating Lactococcus/pMG36e-Usp45-CRAMP in a GM17 liquid medium, culturing the bacteria in a static state overnight, transferring the bacteria to a GM17 liquid medium at a certain ratio, continuing culturing until the bacteria reach a logarithmic growth phase, and directly using the anaculture as an oral vaccine.

In an embodiment, the static culture is performed at a temperature of 28-30° C.

In an embodiment, the transfer is to inoculate L. lactis NZ9000/pMG36e-Usp45-CRAMP in a GM17 medium at a volume ratio of 1:100.

In an embodiment, the OD value of a bacterial culture solution in the logarithmic growth phase is 0.4-0.6.

In an embodiment, the application includes the following steps: inoculating L. lactis NZ9000/pMG36e-Usp45-CRAMP recombinant expression bacteria in a medium containing GM17 at a ratio of 1:100, continuing culturing for 2-3 h until the bacteria reach the logarithmic growth phase ($OD_{600}$=0.4-0.6); culturing the bacteria until the concentration of the recombinant bacteria reach $10^{12}$ CFU/mL, and collecting the induced anaculture as an oral vaccine.

In an embodiment, the application is to culture the L. plantarum, and then use the anaculture of the L. plantarum as an oral vaccine.

In an embodiment, the application is to culture the recombinant L. plantarum, and then use the anaculture of the L. plantarum as an oral vaccine or the main component of an oral vaccine.

In an embodiment, the application includes the following steps: inoculating recombinant L. plantarum/pMG36e-Usp45-Linker-CRAMP in an MRS liquid medium, culturing the bacteria in a static state overnight, transferring the bacteria to an MRS liquid medium at a certain ratio, continuing culturing until the bacteria reach a logarithmic growth phase, and directly using the anaculture as an oral vaccine.

In an embodiment, the static culture is performed at a temperature of 28-30° C.

In an embodiment, the transfer is to inoculate L. plantarum FCQHC24L1/pMG36e-Usp45-Linker-CRAMP in an MRS medium at a volume ratio of (1-10):100.

In an embodiment, the OD value of a bacterial culture solution in the logarithmic growth phase is 0.4-0.6.

In an embodiment, the application includes the following steps: inoculating L. plantarum FCQHC24L1/pMG36e-Usp45-Linker-CRAMP recombinant bacteria in an MRS medium at a volume ratio of (1-10):100, continuing culturing for 2-3 h until the bacteria reach the logarithmic growth phase ($OD_{600}$=0.4-0.6), culturing the bacteria until the concentration of the recombinant bacteria reach $10^{12}$ CFU/mL, and collecting the induced anaculture as an oral vaccine.

The disclosure further claims to protect an application of the L. plantarum in preparation of a medicine for preventing or treating acute colitis.

In an embodiment, the medicine is used in combination with nisin.

In an embodiment, after the medicine is taken into the intestinal tract, nisin or a nisin-containing medicine is then taken to achieve the effect of directional release of CRAMP and increase of the amount of CRAMP secreted in the intestinal tract.

The disclosure further claims to protect an application of the L. lactis and/or L. plantarum in preparation of a product that can be introduced into the intestinal tract; and the product has at least one of the following functions:
 (a) inhibiting intestinal inflammation;
 (b) reconstructing intestinal mucosal barrier;
 (c) improving intestinal mucosal permeability; and
 (d) preventing and treating intestinal inflammation and diseases caused by intestinal inflammation.

The disclosure further claims to protect an application of the L. lactis and/or L. plantarum in preparation of a medicine for preventing or treating inflammatory bowel disease, diarrhea or diseases caused by or related to imbalance of intestinal homeostasis, and the diseases caused by or related to the imbalance of intestinal homeostasis include, but are not limited to, liver diseases, metabolic endocrine diseases, cardiovascular diseases, etc., such as diabetes, pancreatitis, or metabolic syndrome.

The disclosure further claims to protect an application of the L. lactis and/or L. plantarum in preparation of a medicine for preventing or treating acute colitis.

Beneficial effects: (1) The disclosure provides the optimized gene encoding the CRAMP protein, and introduces the Usp45 signal peptide to promote the secretion and expression of CRAMP. The expression level of the CRAMP protein in L. lactis can reach 40 ng/μL, and in L. plantarum can reach 20 ng/μL or even higher. Owing to probiotic properties of L. lactis and L. plantarum, the Lactobacillus expression system becomes a food-grade expression system that can be taken together with bacteria.

(2) The disclosure uses the constructed CRAMP protein-expressing L. lactis and L. plantarum to prepare a vaccine for regulation of intestinal flora disorder, and the L. lactis and L. plantarum have advantages in regulation of intestinal flora and intestinal immune response and maintenance. An anaculture can be directly taken as an oral vaccine to stimulate mice and cause a strong cellular immune response. The recombinant L. lactis can be used as a new oral vaccine product with good industrial prospects, plays a positive role in reducing intestinal inflammation, and has important practical significance for promoting health development of the intestinal tract.

(3) The vaccine containing recombinant L. plantarum and/or L. lactis prepared by the disclosure can specifically regulate intestinal flora disorder, and help regulation of the intestinal flora and intestinal immune response and maintenance. Animal experiments have confirmed that the oral vaccine prepared by the disclosure can stimulate mice and cause a strong cellular immune response. The oral vaccine can be used as a new oral vaccine product with good industrial prospects, plays a positive role in alleviating intestinal inflammation, and has important practical significance in promoting health development of the intestinal tract.

DETAILED DESCRIPTION

The disclosure will be further described below in conjunction with the drawings and specific examples of the specification. These examples are only used to illustrate the disclosure and not to limit the scope of the disclosure. The experimental methods without specific conditions indicated in the following examples usually follow conventional conditions in the field or conditions recommended by manufacturers. Unless otherwise defined, all professional and scientific terms used herein have the same meaning as those familiar to those skilled in the art.

Measurement of mouse weight, colon length, and DAI scores refers to "Curcumin Prevents the Development of Dextran Sulfate Sodium (DSS)-Induced Experimental Colitis".

The qPCR measurement method of ZO-1, ZO-2, occludin, IL-10, IL-113, TNF-α and IL-6 is carried out according to a method in "Neutralization of IL-6 and TNF-α ameliorates intestinal permeability in DSS-induced colitis".

P-ERK, ERK, pp38, p38, p-NF-κB, NF-κB, and CRAMP are measured by Western blot, and the method refers to "Dietary squalene supplementation improves DSS-induced acute colitis by downregulating p38 MAPK and NF-κB signaling pathways".

Example 1 Construction of *L. lactis* NZ9000/pMG36e-Usp45-CRAMP Recombinant Bacteria 1. Construction of Recombinant Plasmid pMG36e-Usp45-CRAMP (1) Codon bias optimization and synthesis of gene sequences: According to the target CRAMP gene sequence, the characteristics of an expression vector pMG36e, as well as a signal peptide sequence Usp45 added for the purpose of high-efficiency secretion and expression, a 228 bp codon-optimized sequence of a Usp45-CRAMP gene was sent to a company for artificial synthesis. XbaI-Usp45-CRAMP-F is a forward primer containing a restriction enzyme site cutting XbaI fused with pMG36e for expression and the first sequence of the 5'end of the signal peptide Usp45-CRAMP, and Usp45-CRAMP-Sph1-R was a reverse primer of the signal peptide Usp45-CRAMP gene. At the same time, primers pNZ1 and pNZ2 for PCR detection and sequencing of recombinant plasmids were also designed based on MCS forward and reverse about 70-90 bp regions of an empty pMG36e plasmid. The optimized and synthesized Usp45-CRAMP sequence is shown in SEQ ID NO: 4; and the optimized and synthesized XbaI-Usp45-CRAMP-F and Usp45-CRAMP-Sph1-R primer sequences are shown in SEQ ID NO: 5-6, respectively.

Figure 1:
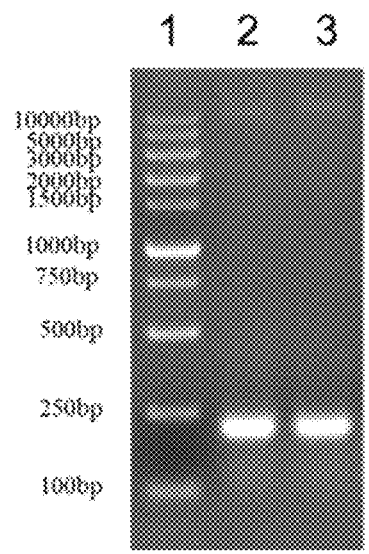
FIG. 1 is the PCR amplification results of CRAMP and Usp45-CRAMP gene fragments; 1 is DL2000 DNA Marker; and 2-3 is the PCR amplification of Usp45-CRAMP gene fragments.

(2) PCR amplification results of a Usp45-CRAMP gene fragment: Using the optimized and synthesized Usp45-CRAMP gene as a template, 1 μL of high-fidelity DNA polymerase KOD-Plus-(1.0 U/4), 1.5 μL of 0.3 μM primers XbaI-Usp45-CRAMP-F and Usp45-CRAMP-Sph1-R each, 1.5 μL of template, 2 μL of 25 mM $MgSO_4$, 5 μL of 2 mM dNTPs, and 5 μL of 10× Buffer for KOD-Plus-were added, and the system was made up to 50 μL with $ddH_2O$. A PCR reaction procedure included: pre-denaturation at 94° C. for 5 min; denaturation at 94° C. for 30 s, annealing at 55° C. for 30 s, extension at 72° C. for 1 min, 35 cycles; and post extension at 72° C. for 10 min. After the PCR reaction, the product was observed and recovered with a 1.0% agarose gel, and an amplified band with a size of about 228 bp was seen, which was consistent with the expected result (FIG. 1). The recovered product would be used as a ligation template to obtain a complete fragment with the added Usp45-CRAMP sequence.

Figure 2:
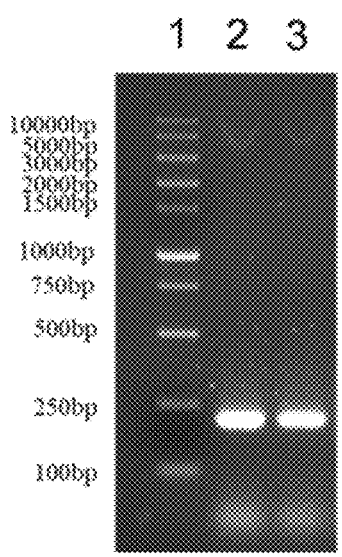
FIG. 2 is the PCR identification results of a recombinant E. coli MC1061/pMG36e-Usp45-CRAMP group; 1 is the DL2000 DNA Marker; 2 is the PCR identification results of the recombinant E. coli MC1061/pMG36e-Usp45-CRAMP group; and 3 is the PCR identification results of a recombinant E. coli MC1061/pNZ8148-Usp45-CRAMP group.

(3) Construction of a recombinant plasmid pMG36e-Usp45-CRAMP: The PCR product recovered in step (2) was subjected to double enzyme digestion with Sph1 and XbaI, and a band with a size of about 228 bp was recovered from the gel. The pMG36e empty plasmid was subjected to double enzyme digestion by the same method, and a band with a size of about 3600 bp was recovered from the gel. 4 μL of the Usp45-CRAMP gene fragment recovered from the gel after the double enzyme digestion and 1 μL of the pMG36e empty plasmid recovered from the gel after the double enzyme digestion were performed. The Usp45-CRAMP and the pMG36e were added at a molar ratio of 6:1, 2 μL of 10× ligation buffer and 1 μL of T4 DNA Ligase (350 U/μL) were added, and the system was made up to 20 μL with $ddH_2O$. After mixing, the system was placed at 4° C. overnight for ligation, and the ligation product was transformed into *E. coli* MC1061 competent cells. In an LB agar culture plate containing 5 μg/mL erythromycin (Er), the cells were cultured at 37° C. for two days, and then a single colony was picked for PCR identification. For PCR identification, the colony to be detected was used as a template, 1 μL of high-fidelity DNA polymerase KOD-Plus-(1.0 U/μl), 1.5 μL of 0.3 μM primers XbaI-Usp45-CRAMP-F and Usp45-CRAMP-Sph1-R each, 1.5 μL of template, 2 μL of 25 mM $MgSO_4$, 5 μL of 2 mM dNTPs, and 5 μL of 10× Buffer for KOD-Plus-were added, and the system was made up to 50 μL with ddH20. A PCR reaction procedure included: pre-denaturation at 94° C. for 5 min; denaturation at 94° C. for 30 s, annealing at 55° C. for 30 s, extension at 72° C. for 1 min, 35 cycles; and post extension at 72° C. for 10 min. After the PCR reaction, the product was observed and recovered with a 1.0% agarose gel, and an amplified band with a size of about 228 bp was seen, which was consistent with the expected result (FIG. 2). Plasmids were extracted from a bacterial culture solution detected as positive with a plasmid DNA extraction kit, and subjected to double enzyme digestion identification and sequencing determination to obtain the recombinant plasmid pMG36e-Usp45-CRAMP.

(4) Preparation of competent cells of *L. lactis*: Cryopreserved *L. lactis* NZ9000 was recovered on a GM17 plate, and a single colony was picked and cultured in a GM17 liquid medium at 30° C. overnight, and then inoculated into 50 mL of a new GM17 liquid medium at a ratio of 1:100 and cultured at 30° C. When the $OD_{500}$ reached 0.3-0.4, the bacterial solution was quickly cooled on ice and centrifuged at 4° C. and 6000×g for 20 min, and the supernatant was discarded. The bacteria were resuspended in 50 mL of a pre-cooled solution containing 0.5 M sucrose and 10% glycerol, the bacterial solution was centrifuged at 4° C. and 6000×g for 20 min, and the supernatant was discarded. The bacteria were resuspended in 25 mL of a pre-cooled solution containing 0.5 M sucrose, 10% glycerol and 50 mM EDTA, the bacterial solution was centrifuged at 4° C. and 6000×g for 15 min, and the supernatant was discarded. The bacteria were resuspended in 15 mL of a pre-cooled solution containing 0.5 M sucrose and 10% glycerol, the bacterial solution was centrifuged at 4° C. and 6000×g for 15 min, and the supernatant was discarded. Finally, the bacteria were resuspended with 500 μL of a pre-cooled solution containing 0.5 M sucrose and 10% glycerol, and the competent cells of *L. lactis* were obtained. 50 μL of the cells were sub-packed per tube and stored at −80° C. for later use.

Figure 3:
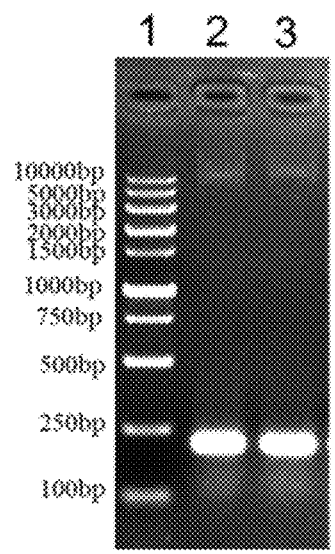
FIG. 3 is the PCR identification results of a recombinant L. lactis NZ9000/pMG36e-Usp45-CRAMP group and a L. lactis NZ9000/pNZ8148-Usp45-CRAMP group; 1 is the DL2000 DNA Marker; 2 is the PCR identification results of CRAMP in the L. lactis NZ9000/pMG36e-Usp45-CRAMP group; and 3 is the PCR identification results of the L. lactis NZ9000/pNZ8148-Usp45-CRAMP group.

(5) Electrotransformation of *L. lactis* and PCR identification of transformants: 50 μL of the *L. lactis* NZ9000 competent cells were thawed on ice, and 1 μL of the recombinant plasmid pMG36e-Usp45-CRAMP constructed in step 1 was added and mixed gently. The above mixture was transferred into an ice-pre-cooled 2 mm cuvette, a single pulse was quickly given, and the parameters were set to 2 kV, 25 F, and 200 Q. Immediately after electric shock, 1 mL of an ice-pre-cooled recovery GM17 medium was gently added, and then the bacterial solution was completely pipetted into a sterile centrifuge tube. A tube cap was tightly closed, and the bacterial solution was placed in an ice bath for 5 min and then cultured in a static state at 30° C. for 2 h. 10 μL, 100 μL, and 900 μL of the bacterial solutions containing the plasmid pMG36e-Usp45-CRAMP were evenly spread on GM17 plates containing 5 μg/mL erythromycin, and cultured in a static state at 30° C. for 1-2 days. A single colony was picked and subjected to PCR identification. The specific operation process is as described in the previous step (2), except that the template is replaced with the recombinant L. lactis bacterial solution to be detected. The PCR product was detected by 1% agarose gel electrophoresis, and an amplified band of about 228 bp was seen (FIG. 3). The positive recombinant expression strain was named L. lactis NZ9000/pMG36e-Usp45-CRAMP.

Example 2 Construction of Recombinant Bacteria L. lactis NZ9000/pNZ8148-Usp45-CRAMP (1) Codon bias optimization and synthesis of gene sequences: According to the method of step 1 (1) of Example 1, the sequence of the Usp45-CRAMP gene as shown in SEQ ID NO: 4 was optimized and synthesized. Sph1-Usp45-CRAMP-F was a forward primer containing a restriction enzyme site cutting XbaI fused with pNZ8148 for expression and the first sequence of the 5'end of the signal peptide Usp45-CRAMP, and Usp45-CRAMP-XbaI-R is a reverse primer of the signal peptide Usp45-CRAMP gene. The optimized and synthesized Sph1-Usp45-CRAMP-F and Usp45-CRAMP-XbaI-R primer sequences were shown in SEQ ID NO: 7-8, respectively.

(2) PCR amplification results of a Usp45-CRAMP gene fragment: The specific implementation mode was the same as that of step 1 (2) of Example 1, except that the primers were replaced with Sph1-Usp45-CRAMP-F and Usp45-CRAMP-XbaI-R. An amplified band with a size of about 228 bp was obtained after amplification and recovery (FIG. 1).

(3) Construction of the recombinant plasmid pNZ8148-Usp45-CRAMP: The specific implementation mode was the same as that of step 1 (3) in Example 1, except that the plasmid pMG36e was replaced with pNZ8148, that is, the pNZ8148 empty plasmid was treated by double enzyme digestion with Sph1 and XbaI, and the plasmid fragment recovered from the gel after double enzyme digestion was ligated with the Usp45-CRAMP gene recovered from the gel after double enzyme digestion. The primers Sph1-Usp45-CRAMP-F and Usp45-CRAMP-XbaI-R were used to carry out colony PCR. After the PCR reaction, the product was observed and recovered with a 1.0% agarose gel, and an amplified band with a size of about 228 bp was seen (FIG. 2). Plasmids were extracted from a bacterial culture solution detected as positive with a plasmid DNA extraction kit, and subjected to double enzyme digestion identification and sequencing determination to obtain the recombinant plasmid pMG36e-Usp45-CRAMP.

(4) Preparation of electroporation competent cells of L. lactis: The specific operation steps are the same as those of step 1 (4) in Example 1.

(5) Electroporation of L. lactis and PCR identification of transformants: The specific operation steps were the same as those in step 1 (5) of Example 1, except that the recombinant plasmid pNZ8148-Usp45-CRAMP was added to the L. lactis NZ9000 competent cells. A single colony after transformation was picked for PCR identification. The specific operation process was as described in step (2) of the present example. The PCR product was detected by 1% agarose gel electrophoresis, and an amplified band of about 228 bp was seen (FIG. 3). The positive recombinant expression strain was named L. lactis NZ9000/pNZ8148-Usp45-CRAMP.

Figure 4:
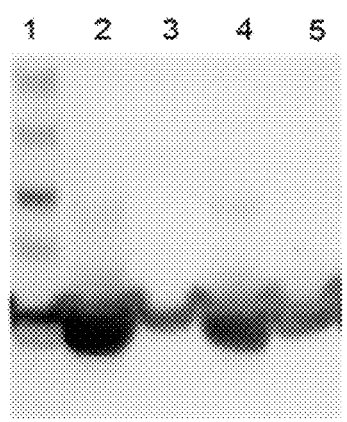
FIG. 4 is the Western blot results of CRAMP in recombinant L. lactis; 1 is protein Marker; 2 is the expression level of CRAMP in the supernatant of a L. lactis NZ9000/pMG36e-Usp45-CRAMP group; 3 is the expression level of CRAMP in the bacteria of the L. lactis NZ9000/pMG36e-Usp45-CRAMP group; 4 is the expression level of CRAMP in the supernatant of a L. lactis NZ9000/pNZ8148-Usp45-CRAMP group; and 5 is the expression level of CRAMP in the bacteria of the L. lactis NZ9000/pNZ8148-Usp45-CRAMP group.

Example 3 Induced Expression of Secretory Recombinant L. lactis Containing CRAMP Gene In Vitro The recombinant expression strain L. lactis NZ9000/pMG36e-Usp45-CRAMP constructed in Example 1 was inoculated in a GM17 liquid medium containing 5 μg/mL erythromycin at a ratio of 1:100, the recombinant strain L. lactis NZ9000/pNZ8148-Usp45-CRAMP constructed in Example 2 was inoculated in a GM17 liquid medium containing 5 μg/mL chloramphenicol at a ratio of 1:100, and the recombinant strains were cultured in a static state at 30° C. overnight. The overnight cultures were inoculated in 10 mL of liquid mediums containing the corresponding antibiotics at a ratio of 1:50, and continued to be cultured for about 2.5 h until the bacteria reached a logarithmic growth phase ($OD_{500}$=0.4-0.6). 40 ng/mL nisin was added to the L. lactis NZ9000/pNZ8148-Usp45-CRAMP culture system for induction for 4 h, the culture system was centrifuged at 4° C. and 10000 rpm for 5 min, and the culture supernatant was collected. After SDS-PAGE electrophoresis and Western blot analysis, the results showed that target bands of 17 KDa were detected in the culture supernatants of the L. lactis NZ9000/pNZ8148-Usp45-CRAMP and L. lactis NZ9000/pMG36e-Usp45-CRAMP (FIG. 4), indicating that the target proteins were secreted and expressed.

Example 4 Application of L. lactis in Preparation of Vaccine

Preparation of recombinant L. lactis NZ9000/pNZ8148-Usp45-CRAMP and L. lactis NZ9000/pMG36e-Usp45-CRAMP for oral vaccines: The recombinant strain L. lactis NZ9000/pMG36e-Usp45-CRAMP constructed in Example 1 was inoculated in a GM17 liquid medium containing 5 μg/mL erythromycin at a volume ratio of 1:100, the recombinant strain L. lactis NZ9000/pNZ8148-Usp45-CRAMP constructed in Example 2 was inoculated in a GM17 liquid medium containing 5 μg/mL chloramphenicol at a volume ratio of 1:100, and the recombinant strains were cultured in a static state at 30° C. overnight. The overnight cultures were inoculated in 10 mL of GM17 liquid mediums containing the corresponding antibiotics at a ratio of 1:100, and continued to be cultured for about 2.5 h until the bacteria reached a logarithmic growth phase (the concentration of the recombinant strain determined by a gradient dilution plate reached $10^{12}$ CFU/mL). Optionally, after the L. lactis NZ9000/pNZ8148-Usp45-CRAMP was cultured to the logarithmic growth phase, nisin was added to induce culture for 2-6 h. At this time, the anacultures were used directly as oral vaccines, or the bacteria were collected by centrifugation and used as the main component of oral vaccines.

Example 5 Application of L. lactis in Preventing Acute Colitis

The oral vaccines containing anacultures of the recombinant L. lactis NZ9000/pNZ8148-Usp45-CRAMP and L. lactis NZ9000/pMG36e-Usp45-CRAMP prepared in Example 4 were applied in prevention of acute colitis. 84 male Balb/c mice aged 6-8 weeks were randomly divided into 6 groups. The first group was a normal saline control group, the second group was an acute colitis model group, the third group was a L. lactis NZ9000/pMG36e group, the fourth group was a *L. lactis* NZ9000/pNZ8148 group, the fifth group was a *L. lactis* NZ9000/pMG36e-Usp45-CRAMP group, and the sixth group was a *L. lactis* NZ9000/pNZ8148-Usp45-CRAMP group (oral administration of vaccines). After one week of pre-feeding and feeding with 3% DSS drinking water for 7 days, oral immunization was carried out by gavage for 4 consecutive days at a dose of 160 μL/mouse. Then the mice were sacrificed at day 10, and the intestinal barrier and inflammation-associated cytokines were determined. The results (FIG. 6-FIG. 13) showed that:

(1) Compared with the 7th day, on the 10th day, the average body weight of mice in each group: increased by 1.084 g in the first group, decreased by 2.19688 g in the second group, decreased by 1.984 g in the third group, decreased by 1.658 g in the fourth group, increased by 0.948 g in the fifth group, and increased by 0.732 g in the sixth group.

(2) The average colon length of each group on the 10th day was: 9.66 cm in the first group, 5.32 cm in the second group, 6.43 cm in the third group, 6.41 cm in the fourth group, 6.88 cm in the fifth group, and 6.86 cm in the sixth group.

(3) The DAI score results of each group on the 10th day were: 0.2 in the first group, 7.2 in the second group, 6.6 in the third group, 6.4 in the fourth group, 4.2 in the fifth group, and 4.0 in the sixth group.

(4) The score results of colon morphology of each group were: 0.2 in the first group, 3.8 in the second group, 3.0 in the third group, 3.4 in the fourth group, 2.4 in the fifth group, and 2.4 in the sixth group.

(5) The changes in colonic tight junction proteins of each group were: compared with the first group, the expression levels of ZO-1 ($p<0.01$), ZO-2 ($p<0.0001$) and occludin ($p<0.0001$) of the second group were significantly decreased; compared with the second group, the expression levels of ZO-1 ($p<0.05$), ZO-2 ($p<0.05$) and occludin ($p<0.05$) of the fifth group were significantly increased; compared with the second group, the expression levels of ZO-1 ($p<0.05$), ZO-2 ($p<0.05$) and occludin ($p<0.05$) of the sixth group were significantly increased; and it can be seen that the oral vaccines can restore the expression levels of ZO-1, ZO-2 and occludin by about 50% relative to the colitis model group.

(6) The changes in colonic inflammatory cytokines of each group were: compared with the first group, IL-6 ($p<0.0001$), IL-1β ($p<0.0001$), and TNF-α ($p<0.0001$) of the second group were significantly increased, and IL-10 ($p<0.0001$) was significantly decreased; compared with the second group, IL-6 ($p<0.05$), IL-1β ($p<0.05$), and TNF-α ($p<0.05$) of the fifth group were significantly decreased, and IL-10 ($p<0.05$) was significantly increased; compared with the second group, IL-6 ($p<0.05$), IL-1β ($p<0.05$), and TNF-α ($p<0.01$) of the sixth group were significantly decreased, and IL-10 ($p<0.05$) was significantly increased; and it can be seen that the oral vaccines can reduce the levels of the inflammatory cytokines IL-6, IL-1β, and TNF-α by 30-50% relative to the colitis model group, and at least double IL-10.

(7) The changes in protein levels of key colonic transcription factors in each group were: compared with the first group, p-ERK/ERK ($p<0.01$), p-p38/p38 ($p<0.01$) and p-NF-κB/NF-κB ($p<0.01$) of the second group were significantly increased; compared with the second group, p-p38/p38 ($p<0.05$) and p-NF-κB/NF-κB ($p<0.05$) of the fifth group were significantly decreased, and there was no significant difference in p-ERK/ERK ($p>0.05$); and compared with the second group, p-ERK/ERK ($p<0.05$), p-p38/p38 ($p<0.05$) and p-NF-κB/NF-κB ($p<0.05$) of the sixth group were significantly decreased.

The above results show that the application of oral vaccines containing the *L. lactis* NZ9000/pMG36e-Usp45-CRAMP or the *L. lactis* NZ9000/pNZ8148-Usp45-CRAMP can restore the intestinal barrier, reduce inflammatory cell infiltration, inhibit secretion of inflammatory cytokines, and have a good recovery effect.

The inventor also tried to use *L. lactis* NZ9000/pNZ8148-Usp45-CRAMP in combination with nisin. For example, after mice were subjected to gavage with the *L. lactis* NZ9000/pMG36e-Usp45-CRAMP not induced by nisin for a period of time to make the *L. lactis* NZ9000/pMG36e-Usp45-CRAMP colonize in the intestinal tract, the treated subjects were then administered with nisin or a product with a nisin content, thereby achieving the effect of timed and directional release of CRAMP in the intestinal tract.

Comparative Example 1 Secretory Recombinant *L. lactis* Containing CRAMP Gene

Taking the secretory recombinant *L. lactis* containing CRAMP gene in the prior art as a control, the CRAMP gene (GGACTTCTCCGCAAAGGTGGGGAGAAGATTGGT-GAAAAGCTTAAGAAAATTGG CCAGAAAAT-TAAGAAT-TTTTTTCAGAAACTTGTACCTCAGCCAGAG, SEQ ID NO: 14) expressed thereof was not codon-optimized and could not promote intracellular self-cleavage of the Usp45 signal peptide and CRAMP gene or promote extracellular secretion of CRAMP, the content of CRAMP protein secreted in the supernatant was low, and the expression product was about 1.5 ng/μL.

Figure 5:
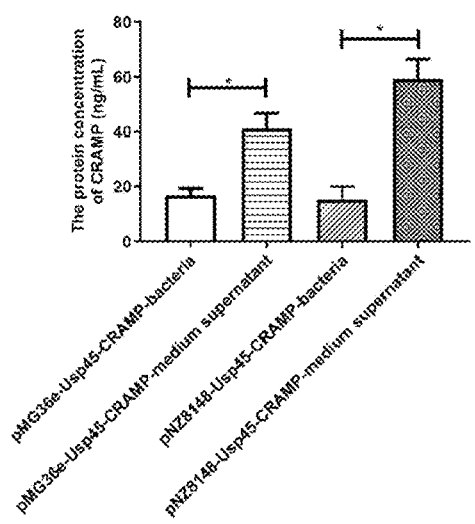
FIG. 5 is the ELISA results of recombinant CRAMP-encoding L. lactis.
Figure 6:
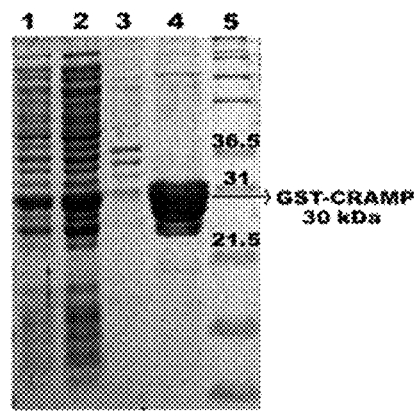
FIG. 6 is the expression of CRAMP in E. coli by previous studies; 1 is the expression of CRAMP in an E. coli lysate; 2 is the expression of CRAMP in the supernatant of the E. coli lysate; 3 is the expression of CRAMP in the precipitation of the E. coli lysate; 4 is the expression of CRAMP in a GST-CRAMP elution buffer on an elution column; and 5 is the protein Marker.
Figure 7:
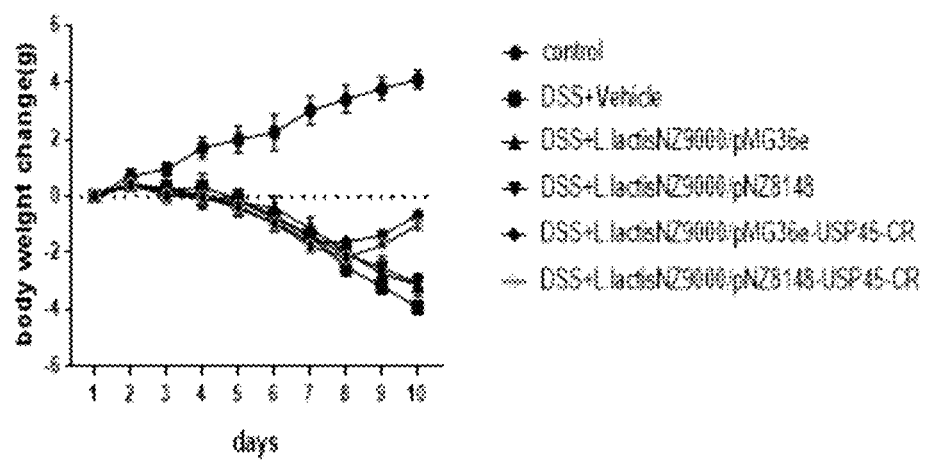
FIG. 7 is changes in the body weight of mice in each group during the construction of colitis animal models.
Figure 8A:
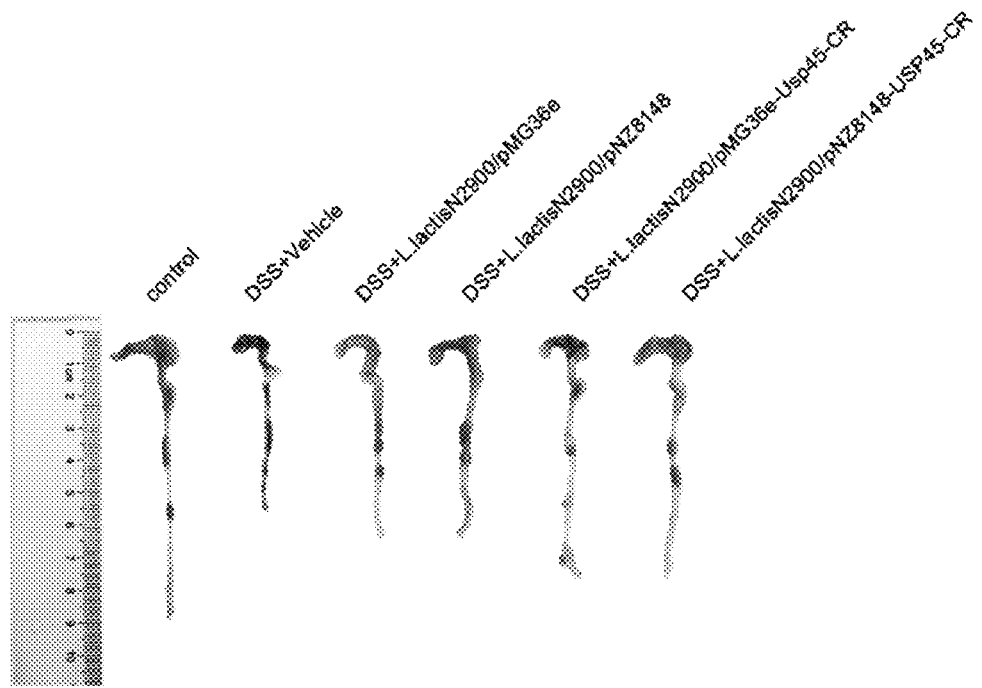
FIG. 8A is a comparison of the colon length of mice in each group (A).
Figure 8B:
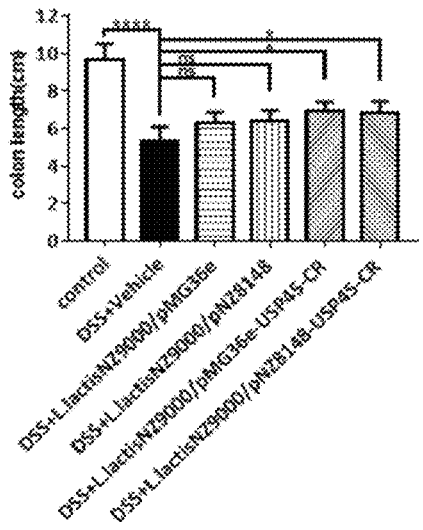
FIG. 8B is a statistical diagram of the colon length of each group.
Figure 9:
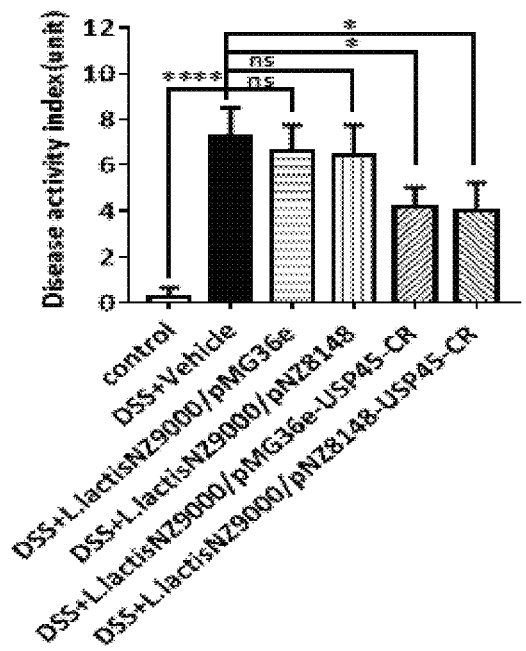
FIG. 9 is the scores of clinical indicators of colitis.
Figure 10:
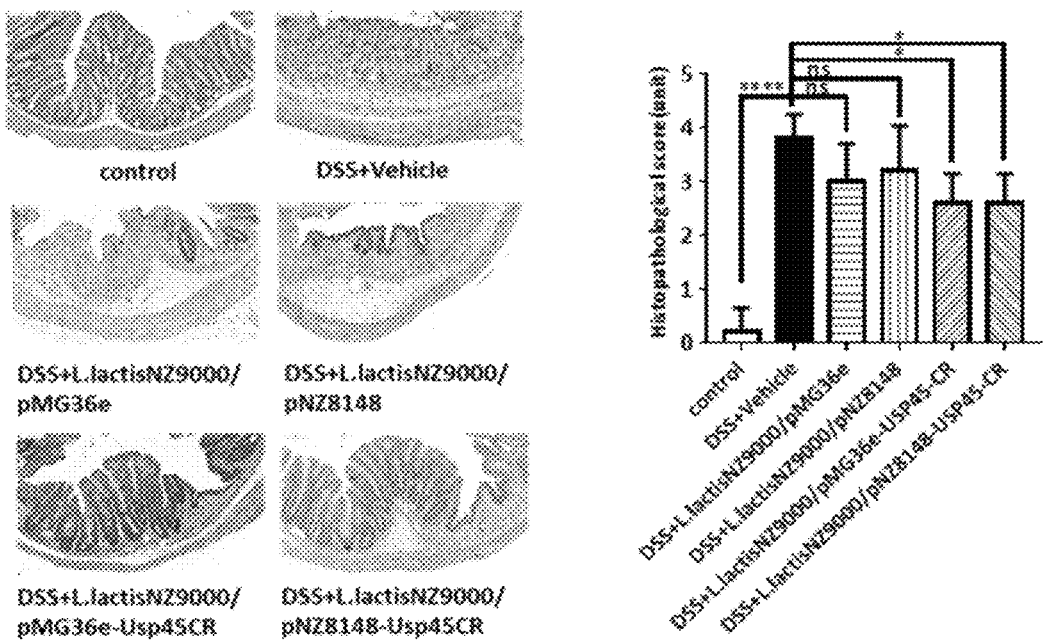
FIG. 10 is the observation and scoring of the histopathological morphology of the colon.
Figure 11A:
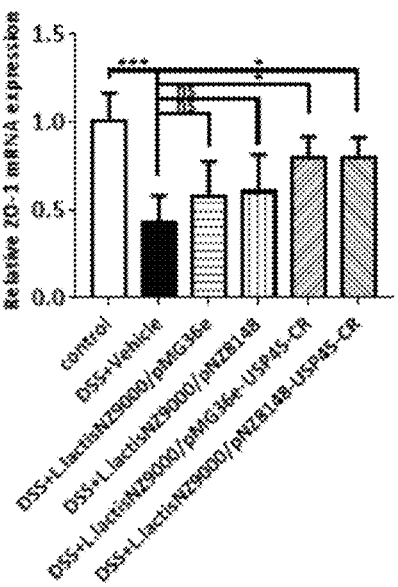
FIG. 11A is changes in an intestinal tight junction protein ZO-1 measured by qPCR.
Figure 11B:
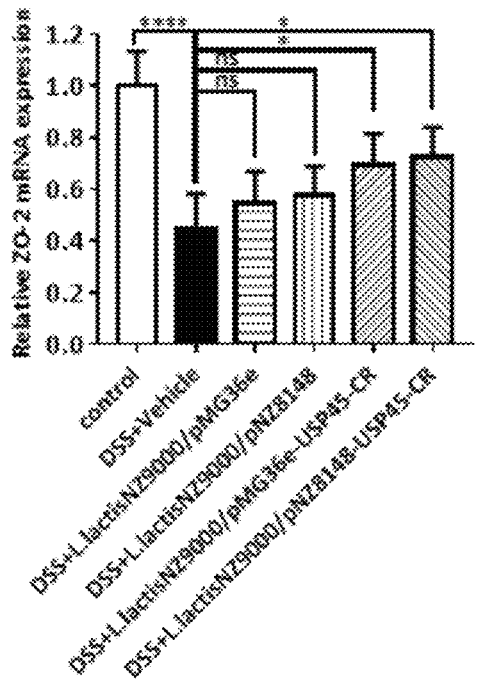
FIG. 11B is changes in an intestinal tight junction protein ZO-2 measured by qPCR.
Figure 11C:
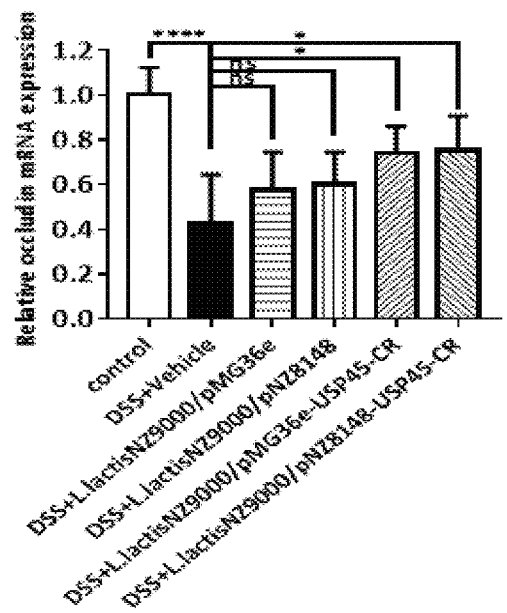
FIG. 11C is changes in an intestinal tight junction protein occludin measured by qPCR.
Figure 12A:
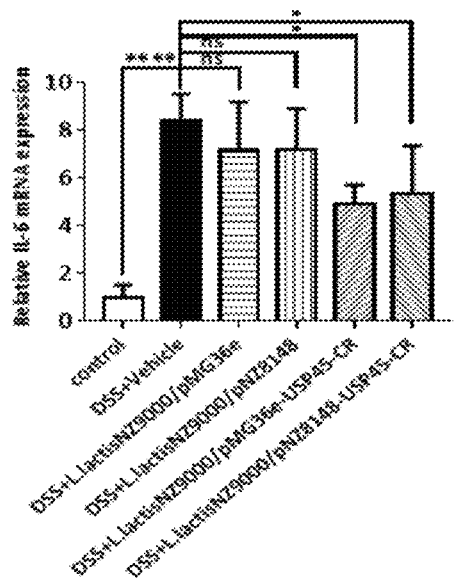
FIG. 12A is the expression of inflammatory cytokine IL-6 measured by qPCR.
Figure 12B:
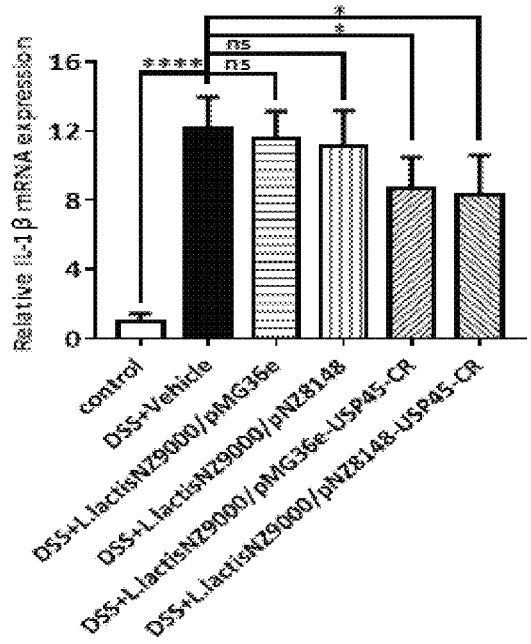
FIG. 12B is the expression of inflammatory cytokine IL-1β measured by qPCR.
Figure 12C:
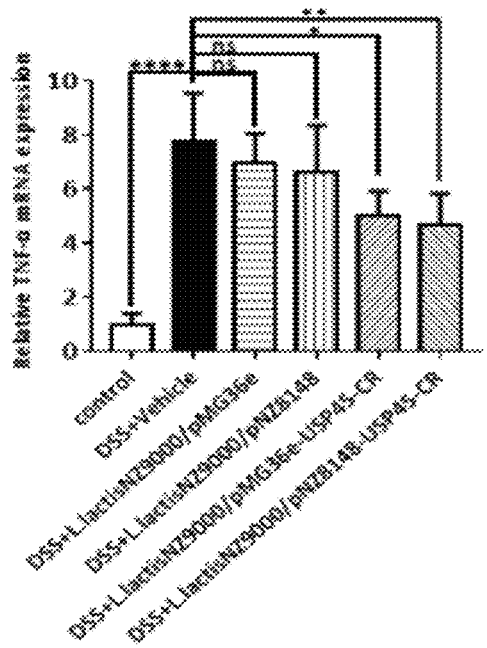
FIG. 12C is the expression of inflammatory cytokine TNF-α measured by qPCR.
Figure 12D:
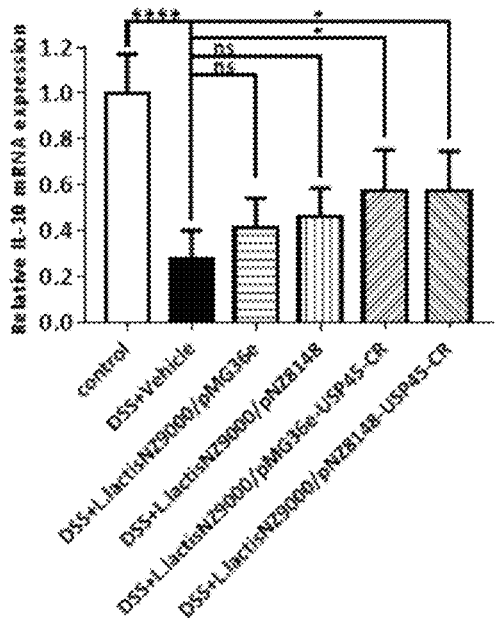
FIG. 12D is the expression of anti-inflammatory cytokine IL-10 measured by qPCR.
Figure 13A:
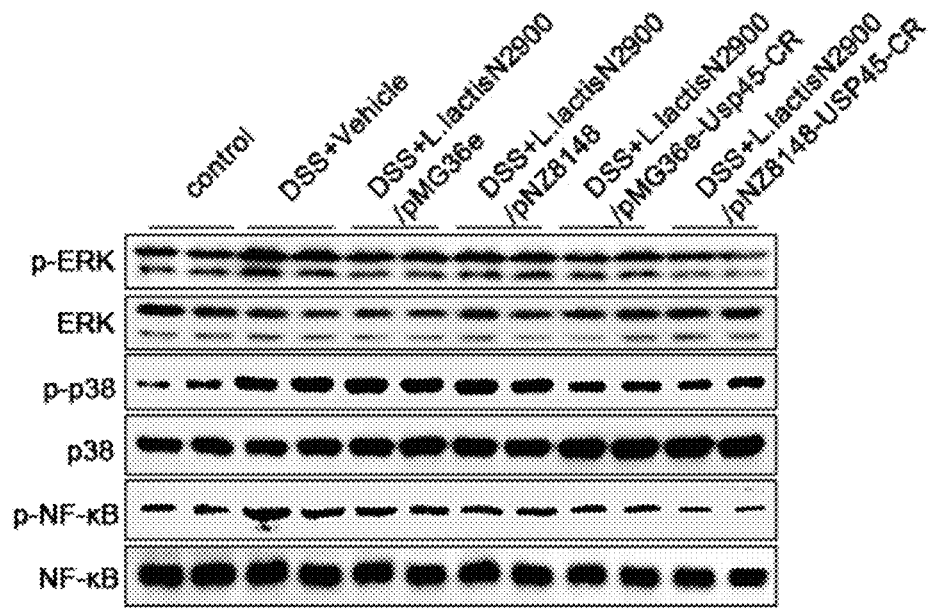
FIG. 13A is changes in phosphorylation levels of inflammation signaling pathway key transcription factors p-ERK, ERK, p-p38, p38, p-NF-κB and NF-κB measured by Western blot.
Figure 13B:
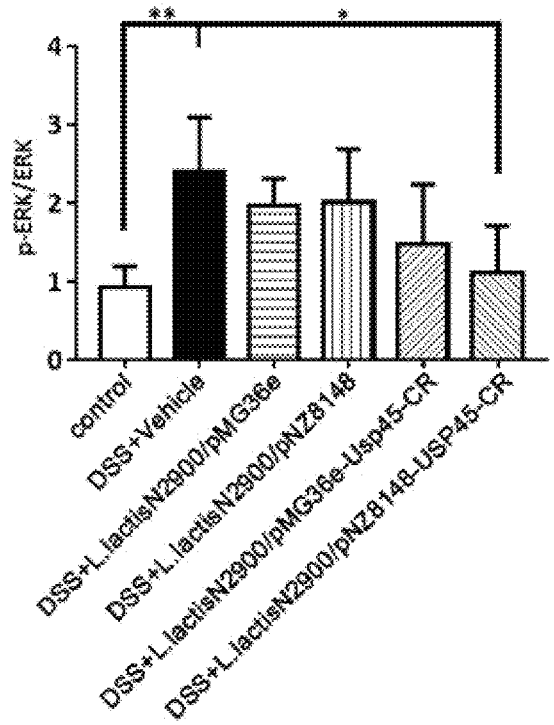
FIG. 13B is changes in the phosphorylation levels of the inflammation signaling pathway key transcription factors p-ERK/ERK measured by Western blot.
Figure 13C:
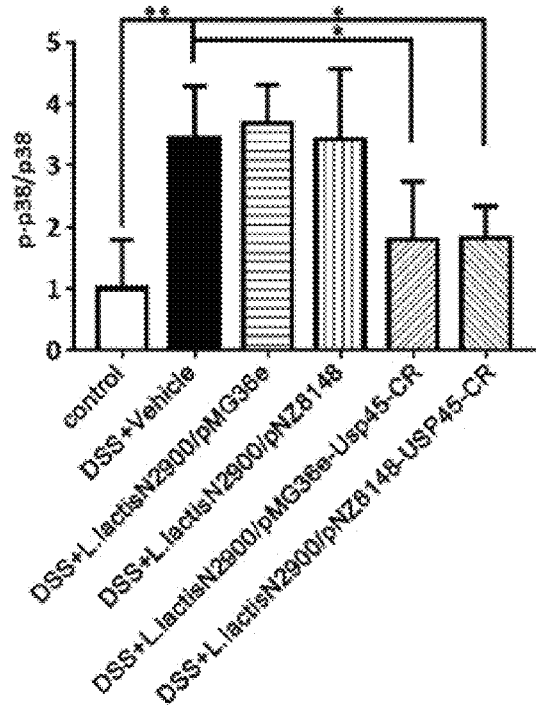
FIG. 13C is changes in the phosphorylation levels of the inflammation signaling pathway key transcription factors p-p38/p38 measured by Western blot.
Figure 13D:
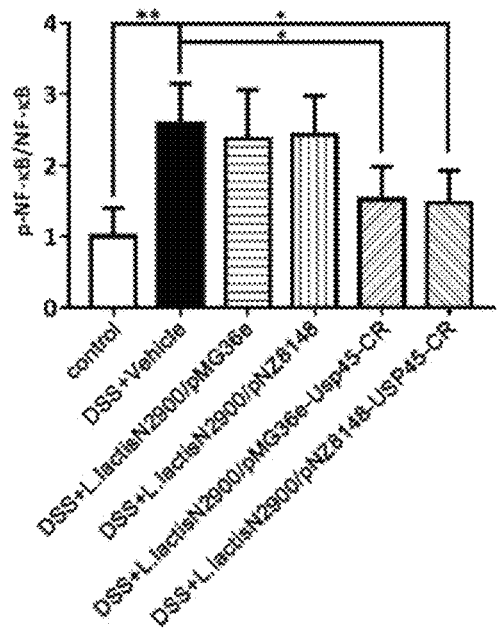
FIG. 13D is changes in the phosphorylation levels of the inflammation signaling pathway key transcription factors p-NF-κB/NF-κB measured by Western blot.

The ability of the recombinant strain constructed in Comparative Example 1 and Examples 1 and 2 to express CRAMP was examined by ELISA, and the results showed that (FIG. 5) the expression levels of CRAMP proteins of the recombinant strain *L. lactis* NZ9000/pMG36e-Usp45-CRAMP and *L. lactis* NZ9000/pNZ8148-Usp45-CRAMP were about 20 ng/μL, which was 13 times higher than that in the prior art (1.5 ng/4); the level of extracellular protein secreted by the recombinant strain *L. lactis* NZ9000/pMG36e-Usp45-CRAMP was about 40 ng/μL, which was 27 times higher than the expression level in the comparative example (1.5 ng/4); and the expression level of extracellular CRAMP protein secreted by the recombinant strain *L. lactis* NZ9000/pNZ8148-Usp45-CRAMP was about 60 ng/μL, which was 40 times higher than that in Comparative Example 1 (1.5 ng/4).

Example 6 Construction of Recombinant Plasmid pMG36e-CRAMP (1) Codon bias optimization and synthesis of gene sequences: According to the target CRAMP gene sequence and the characteristics of an expression vector pMG36e, a 108 bp codon-optimized sequence of a CRAMP gene was sent to a company for artificial synthesis. XbaI-CRAMP-F was a forward primer containing a restriction enzyme site cutting XbaI (TCTAGA) fused with pMG36e for expression and the first sequence of the 5'end of the signal peptide CRAMP, and CRAMP-Sph1-R is a CRAMP gene reverse primer containing a restriction enzyme site cutting Sph1 (GCATGC). The optimized and synthesized CRAMP sequence was shown in SEQ ID NO: 1; and the optimized and synthesized XbaI-CRAMP-F and CRAMP-Sph1-R primer sequences were shown in SEQ ID NO: 11 and SEQ ID NO: 6, respectively.

(2) PCR amplification results of a CRAMP gene fragment: The specific operation was the same as that of step 1 (2) of Example 1.

Figure 15:
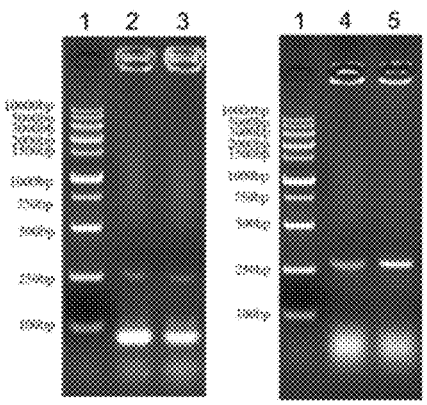
FIG. 15 is the PCR identification results of a recombinant E. coli MC1061/pMG36e-Usp45-Linker-CRAMP group; 1 is the DL2000 DNA Marker; 2-3 is the PCR identification results of a recombinant E. coli MC1061/pMG36e-CRAMP group; and 4-5 is the PCR identification results of the recombinant E. coli MC1061/pMG36e-Usp45-Linker-CRAMP group.

(3) Construction of the recombinant plasmid pMG36e-CRAMP: The specific operation was the same as that of step 1 (3) in Example 1, except that after double enzyme digestion, a band of about 102 bp was recovered from the gel. The primers XbaI-CRAMP-F and CRAMP-Sph1-R were used for carrying out colony PCR. After the PCR reaction, the product was observed and recovered with a 1.0% agarose gel, and an amplified band with a size of about 102 bp was seen (FIG. 15), which was consistent with the expected result. Plasmids were extracted from a bacterial culture solution detected as positive with a plasmid DNA extraction kit, and subjected to double enzyme digestion identification and sequencing determination to obtain the recombinant plasmid pMG36e-CRAMP.

Example 7 Construction of Recombinant Plasmid pNZ8148-CRAMP (1) Codon bias optimization and synthesis of gene sequences: The nucleotide sequence of the CRAMP gene was synthesized according to the method of step (1) in Example 6. Sph1-CRAMP-F was a forward primer containing a restriction enzyme site cutting Sph1 (GCATGC) fused with pMG36e for expression and the first sequence of the 5'end of the signal peptide CRAMP, and CRAMP-XbaI-R was a CRAMP gene reverse primer containing a restriction enzyme site cutting XbaI (TCTAGA). The optimized and synthesized Sph1-CRAMP-F and CRAMP-XbaI-R primer sequences were shown in SEQ ID NO: 12 and SEQ ID NO: 8, respectively.

Figure 14:
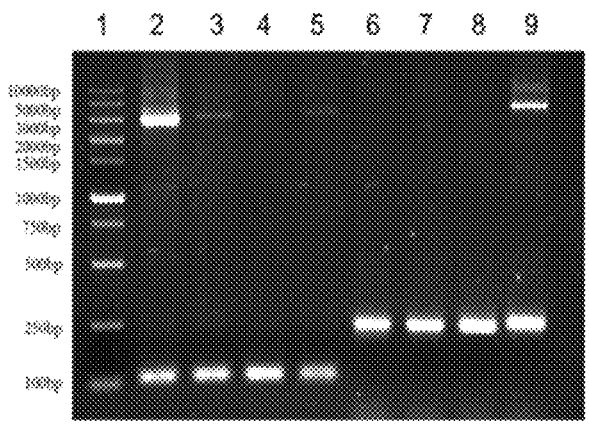
FIG. 14 is the PCR amplification results of CRAMP and Usp45-Linker-CRAMP gene fragments; 1 is DL2000 DNA Marker; 2-5 is the PCR amplification results of the CRAMP gene fragment; and 6-9 is the PCR amplification results of the Usp45-Linker-CRAMP gene fragment.

(2) PCR amplification results of a CRAMP gene fragment: The optimized and synthesized CRAMP gene was used as a template, and the primers Sph1-CRAMP-F and CRAMP-XbaI-R were used for PCR amplification. The PCR system and reaction conditions were the same as those in step 1 (2) of Example 1. After the PCR reaction, the product was observed and recovered with a 1.0% agarose gel, and an amplified band with a size of about 102 bp was seen, which was consistent with the expected result (FIG. 14). The recovered product would be used as a ligation template to obtain a complete fragment with the added Sph1-CRAMP-XbaI sequence.

(3) Construction of recombinant plasmid pNZ8148-CRAMP: The specific operation was the same as that of the step (3) in Example 6. The pNZ8148 was subjected to double enzyme digestion with XbaI and Sph1, and a band with a size of about 3100 bp was recovered from the gel. The CRAMP gene fragment recovered from the gel after double enzyme digestion and the pMG36e empty plasmid recovered from the gel after double enzyme digestion were ligated and recovered. After transformation into E. coli MC1061 competent cells, PCR verification of the colony was carried out. After the PCR reaction, the product was observed and recovered with a 1.0% agarose gel, and an amplified band with a size of about 102 bp was seen (FIG. 15), which was consistent with the expected result. Plasmids were extracted from a bacterial culture solution detected as positive with a plasmid DNA extraction kit, and subjected to double enzyme digestion identification and sequencing determination to obtain the recombinant plasmid pNZ8148-CRAMP.

Example 8 Construction of Recombinant Plasmid pMG36e-Usp45-Linker-CRAMP (1) Codon bias optimization and synthesis of gene sequences: According to the target CRAMP gene sequence, the characteristics of an expression vector pMG36e, as well as a signal peptide sequence Usp45 added for the purpose of high-efficiency secretion and expression, a 243 bp codon-optimized sequence of a Usp45-Linker-CRAMP gene was sent to a company for artificial synthesis. XbaI-Usp45-Linker-CRAMP-F was a forward primer containing a restriction enzyme site cutting XbaI fused with pMG36e for expression and the first sequence of the 5'end of the signal peptide Usp45-Linker-CRAMP, and Usp45-Linker-CRAMP-Sph1-R was a reverse primer of the signal peptide Usp45-Linker-CRAMP gene. At the same time, the primers pNZ1 and pNZ2 for PCR detection and sequencing of recombinant plasmids were also designed based on MCS forward and reverse about 70-90 bp regions of an empty pMG36e plasmid. The optimized and synthesized Usp45-Linker-CRAMP sequence was shown in SEQ ID NO: 10; and the optimized and synthesized XbaI-Usp45-Linker-CRAMP-F and Usp45-Linker-CRAMP-Sph1-R primer sequences were shown in SEQ ID NO: 5-6, respectively.

(2) PCR amplification results of a Usp45-Linker-CRAMP gene fragment: The specific operation steps were the same as those in step 1 (2) of Example 1, except that the optimized and synthesized Usp45-Linker-CRAMP gene was used as a template, and the primers XbaI-Usp45-Linker-CRAMP-F and Usp45-Linker-CRAMP-Sph1-R were used to amplify the Usp45-Linker-CRAMP gene fragment. After the PCR reaction, the product was observed and recovered with a 1.0% agarose gel, and an amplified band with a size of about 243 bp was seen, which was consistent with the expected result (FIG. 14). The recovered product would be used as a ligation template to obtain a complete fragment with the added Usp45-Linker-CRAMP sequence.

(3) Construction of the recombinant plasmid pMG36e-Usp45-Linker-CRAMP: The PCR product recovered in step (2) of the present example was subjected to double enzyme digestion with Sph1 and XbaI, and a band with a size of about 243 bp was recovered from the gel. The plasmid was subjected to double enzyme digestion according to the method of step 1 (3) in Example 1, and the plasmid fragment after digestion and recovery was ligated with the Usp45-Linker-CRAMP recovered from the gel. The ligation product was transformed into E. coli MC1061 competent cells, and transformants were cultured. The primers XbaI-Usp45-Linker-CRAMP-F and Usp45-Linker-CRAMP-Sph1-R were used for PCR verification of a colony. After the PCR reaction, the product was observed and recovered with a 1.0% agarose gel, and an amplified band with a size of about 243 bp was seen (FIG. 15), which was consistent with the expected result. Plasmids were extracted from a bacterial culture solution detected as positive with a plasmid DNA extraction kit, and subjected to double enzyme digestion identification and sequencing determination to obtain the recombinant plasmid pMG36e-Usp45-Linker-CRAMP.

Example 9 Construction of Recombinant Plasmid pNZ8148-Usp45-Linker-CRAMP (1) Codon bias optimization and synthesis of gene sequences: The Usp45-Linker-CRAMP gene was designed and synthesized according to the method of Example 8. Sph1-Usp45-Linker-CRAMP-F was a forward primer containing a restriction enzyme site cutting XbaI fused with pNZ8148 for expression and the first sequence of the 5'end of the signal peptide Usp45-Linker-CRAMP, and Usp45-Linker-CRAMP-XbaI-R was a reverse primer of the Usp45-Linker-CRAMP gene. The optimized and synthesized Sph1-Usp45-Linker-CRAMP-F and Usp45-Linker-CRAMP-XbaI-R primer sequences were shown in SEQ ID NO: 7-8, respectively.

(2) PCR amplification results of a Usp45-Linker-CRAMP gene fragment: The Usp45-Linker-CRAMP gene fragment was amplified according to the method of Example 8, except that the primers were Sph1-Usp45-Linker-CRAMP-F and Usp45-Linker-CRAMP-XbaI-R. The PCR reaction result was consistent with the expected result (FIG. 14), and the recovered product would be used as a ligation template to obtain a complete fragment with the added Usp45-Linker-CRAMP sequence.

(3) Construction of the recombinant plasmid pNZ8148-Usp45-Linker-CRAMP: The specific operation steps were the same as those in Example 8, except that the plasmid was replaced with pNZ8148. The primers used for colony PCR are Sph1-Usp45-Linker-CRAMP-F and Usp45-Linker-CRAMP-XbaI-R. After the PCR reaction, the product was observed and recovered with a 1.0% agarose gel, and an amplified band with a size of about 243 bp was seen (FIG. 15), which was consistent with the expected result. Plasmids were extracted from a bacterial culture solution detected as positive with a plasmid DNA extraction kit, and subjected to double enzyme digestion identification and sequencing determination to obtain the recombinant plasmid pMG36e-Usp45-Linker-CRAMP.

Example 10 Construction of Secretory Recombinant *L. plantarum* Containing CRAMP Gene (1) Preparation of electrotransformed competent cells of *L. plantarum*: Cryopreserved *L. plantarum* FCQHC24L1 was recovered on an MRS plate, and a single colony was picked and cultured in an MRS liquid medium at 30° C. overnight, and then inoculated into 50 mL of a new MRS liquid medium at a ratio of 1:100 and cultured at 30° C. When the $OD_{500}$ reached 0.3-0.4, the bacterial solution was quickly cooled on ice and centrifuged at 4° C. and 6000×g for 20 min, and the supernatant was discarded. The bacteria were resuspended in 50 mL of a pre-cooled solution containing 0.5 M sucrose and 10% glycerol, the bacterial solution was centrifuged at 4° C. and 6000×g for 20 min, and the supernatant was discarded. The bacteria were resuspended in 25 mL of a pre-cooled solution containing 0.5 M sucrose, 10% glycerol and 50 mM EDTA, the bacterial solution was centrifuged at 4° C. and 6000×g for 15 min, and the supernatant was discarded. The bacteria were resuspended in 15 mL of a pre-cooled solution containing 0.5 M sucrose and 10% glycerol, the bacterial solution was centrifuged at 4° C. and 6000×g for 15 min, and the supernatant was discarded. Finally, the bacteria were resuspended with 500 μL of a pre-cooled solution containing 0.5 M sucrose and 10% glycerol, and the bacteria are *L. plantarum* competent cells. 50 μL of the cells were sub-packed per tube and stored at −80° C. for later use.

Figure 16:
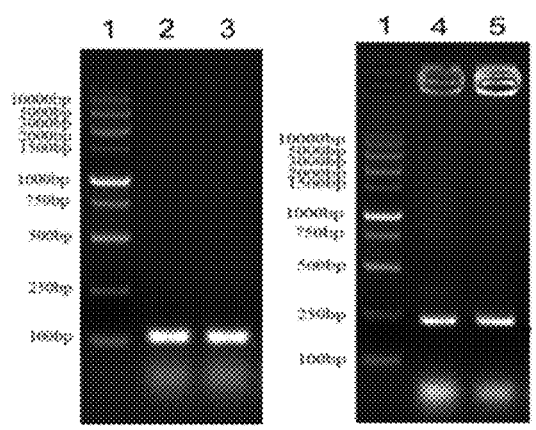
FIG. 16 is the PCR identification results of L. plantarum FCQHC24L1/pMG36e-CRAMP, L. plantarum FCQHC24L1/pNZ81848-CRAMP, L. plantarum FCQHC24L1/pMG36e-Usp45-Linker-CRAMP, and L. plantarum FCQHC24L1 L1/pNZ8148-Usp45-Linker-CRAMP. 1 is the DL2000 DNA Marker; 2 is the PCR identification results of CRAMP in the L. plantarum FCQHC24L1/pMG36e-CRAMP; 3 is the PCR identification results of CRAMP in the L. plantarum FCQHC24L1/pNZ8148-CRAMP; 4 is the PCR identification results of Usp45-Linker-CRAMP in the L. plantarum FCQHC24L1/pMG36e-Usp45-Linker-CRAMP; and 5 is the PCR identification results of the L. plantarum FCQHC24L1/pNZ8148-Usp45-Linker-CRAMP.

(2) Electrotransformation of *L. plantarum* and PCR identification of transformants: 50 μL of *L. plantarum* FCQHC24L1 competent cells were thawed on an ice bath, and 1 μL of the recombinant plasmid pMG36e-CRAMP constructed in Example 6, the recombinant plasmid pNZ8148-CRAMP constructed in Example 7, the recombinant plasmid pMG36e-Usp45-Linker-CRAMP constructed in Example 8, and the recombinant plasmid pNZ8148-Usp45-Linker-CRAMP constructed in Example 9 were added respectively and mixed gently. The above mixtures were transferred into an ice-pre-cooled 2 mm cuvette, a single pulse was quickly given, and the parameters were set to 2 kV, 25 F, and 200 Q. Immediately after electroporation, 1 mL of an ice-pre-cooled recovery MRS medium was gently added, and then the bacterial solution was completely pipetted into a sterile centrifuge tube. A tube cap was tightly closed, and the bacterial solution was placed in an ice bath for 5 min and then cultured in a static state at 30° C. for 2 h. 10 μL, 100 μL, and 900 μL of the bacterial solutions containing the plasmid pMG36e-CRAMP or the plasmid pMG36e-Usp45-Linker-CRAMP were evenly spread on MRS plates containing 5 μg/mL erythromycin, and 10 μL, 100 μL, and 900 μL of the bacterial culture solutions containing the plasmid pNZ8148-CRAMP or the plasmid pNZ8148-Usp45-Linker-CRAMP were evenly spread on M17 plates containing 5 μg/mL chloramphenicol, and cultured in a static state at 30° C. for 1-2 days. A single colony was picked and subjected to PCR identification. The PCR product was detected by 1% agarose gel electrophoresis, and an amplified band of about 243 bp was seen (FIG. 16). The positive recombinant expression strains were named *L. plantarum* FCQHC24L1/pMG36e-CRAMP, *L. plantarum* FCQHC24L1/pNZ8148-CRAMP, *L. plantarum* FCQHC24L1/pNZ8148-Usp45-Linker-CRAMP and *L. plantarum* FCQHC24L1/pMG36e-Usp45-Linker-CRAMP.

Figure 17:
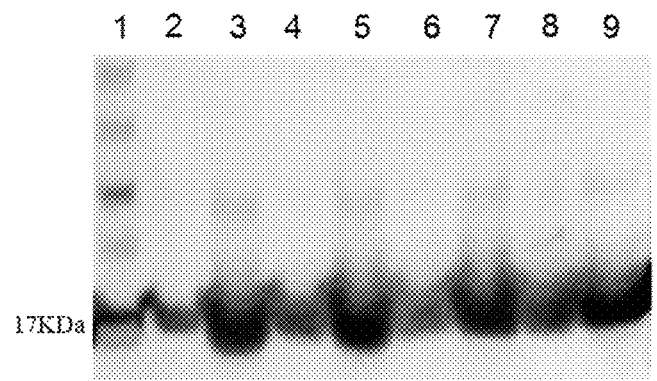
FIG. 17 is the Western blot results of CRAMP in recombinant L. plantarum; 1 is the protein Marker; 2 is the expression level of CRAMP in the bacteria of the L. plantarum FCQHC24L1/pMG36e-CRAMP; 3 is the expression level of CRAMP in the supernatant of the L. plantarum FCQHC24L1/pMG36e-CRAMP; 4 is the expression level of CRAMP in the bacteria of the L. plantarum FCQHC24L1/pNZ81848-CRAMP; 5 is the expression level of CRAMP in the supernatant of the L. plantarum FCQHC24L1/pNZ81848-CRAMP; 6 is the expression level of CRAMP in the bacteria of the L. plantarum FCQHC24L1/pMG36e-Usp45-Linker-CRAMP; 7 is the expression level of CRAMP in the supernatant of the L. plantarum FCQHC24L1/pMG36e-Usp45-Linker-CRAMP; 8 is the expression level of CRAMP in the bacteria of the L. plantarum FCQHC24L1/pNZ8148-Usp45-Linker-CRAMP; and 9 is the expression level of CRAMP in the supernatant of the L. plantarum FCQHC24L1/pNZ8148-Usp45-Linker-CRAMP.

Example 11 Induced Expression of Secretory Recombinant *L. plantarum* Containing CRAMP Gene In Vitro The recombinant strain *L. plantarum* FCQHC24L1/pMG36e-CRAMP and *L. plantarum* FCQHC24L1/pMG36e-Usp45-Linker-CRAMP were respectively inoculated in MRS liquid mediums containing 5 μg/mL erythromycin at a ratio of 1:100. The recombinant strain *L. plantarum* FCQHC24L1/pNZ8148-CRAMP and the recombinant strain *L. plantarum* FCQHC24L1/pNZ8148-Usp45-Linker-CRAMP were respectively inoculated in MRS liquid mediums containing 5 μg/mL chloramphenicol at a ratio of 1:100, and the recombinant strains were cultured in a static state at 30° C. overnight. The overnight cultures were respectively inoculated in 10 mL of liquid mediums containing the corresponding antibiotics at a ratio of 1:50, and continued to be cultured for about 2.5 h until the bacteria reached a logarithmic growth phase ($OD_{500}$=0.4-0.6). 40 ng/mL nisin was added to the culture systems of the recombinant strain *L. plantarum* FCQHC24L1/pNZ8148-CRAMP and *L. plantarum* FCQHC24L1/pNZ8148-Usp45-Linker-CRAMP for induction for 4 h, the culture systems were centrifuged at 4° C. and 10000 rpm for 5 min, and the culture supernatants were collected. After SDS-PAGE electrophoresis and Western blot analysis, the results showed that target bands of 17 KDa were detected in the culture supernatants of the *L. plantarum* FCQHC24L1/pMG36e-CRAMP, the *L. plantarum* FCQHC24L1/pNZ8148-CRAMP, the *L. plantarum* FCQHC24L1/pNZ8148-Usp45-Linker-CRAMP and the *L. plantarum* FCQHC24L1/pMG36e-Usp45-Linker-CRAMP (FIG. 17), indicating that the target proteins were secreted and expressed.

Example 12 Application of *L. plantarum* in Preparation of Vaccines

Preparation of recombinant *L. plantarum* oral vaccines of *L. plantarum* FCQHC24L1/pMG36e-CRAMP, *L. plantarum* FCQHC24L1/pNZ8148-CRAMP, *L. plantarum* FCQHC24L1/pNZ8148-Usp45-Linker-CRAMP and *L. plantarum* FCQHC24L1/pMG36e-Usp45-Linker-CRAMP: The recombinant strain *L. plantarum* FCQHC24L1/pMG36e-CRAMP and the recombinant strain *L. plantarum* FCQHC24L1/pMG36e-Usp45-Linker-CRAMP were respectively inoculated in MRS liquid mediums at a volume ratio of 1:100, the recombinant strain *L. plantarum* FCQHC24L1/pNZ8148-CRAMP and the recombinant strain *L. plantarum* FCQHC24L1/pNZ8148-Usp45-Linker-CRAMP were respectively inoculated in MRS liquid mediums at a volume ratio of 1:100, and the recombinant strains were cultured at 30° C. overnight. The overnight cultures were inoculated in 10 mL of MRS liquid mediums containing the corresponding antibiotics at a ratio of 1:100, and continued to be cultured for about 2.5 h until the bacteria reached a logarithmic growth phase (the concentration of the recombinant strain determined by a gradient dilution plate reached $10^{12}$ CFU/mL). Optionally, after the *L. plantarum* FCQHC24L1/pNZ8148-CRAMP and the *L. plantarum* FCQHC24L1/pNZ8148-Usp45-Linker-CRAMP were cultured to the logarithmic growth phase, nisin was added to induce culture for 2-6 h. At this time, the anacultures were used directly as oral vaccines, or the bacteria were collected by centrifugation and used as the main component of oral vaccines.

Example 13 Application of *L. plantarum* in Prevention of Acute Colitis

The oral vaccines containing the anacultures of the recombinant *L. plantarum* FCQHC24L1/pMG36e-CRAMP, *L. plantarum* FCQHC24L1/pNZ8148-CRAMP, *L. plantarum* FCQHC24L1/pNZ8148-Usp45-Linker-CRAMP and *L. plantarum* FCQHC24L1/pMG36e-Usp45-Linker-CRAMP prepared in Example 11 were applied to prevent acute colitis.

84 male Balb/c mice aged 6-8 weeks were randomly divided into 10 groups. The first group was a normal saline control group, the second group was an acute colitis model group, the third group was a *L. plantarum* FCQHC24L1/pMG36e group, the fourth group was a *L. plantarum* FCQHC24L1/pNZ8148 group, the fifth group was a *L. plantarum* FCQHC24L1/pMG36e-CRAMP group, the sixth group was a *L. plantarum* FCQHC24L1/pNZ8148-CRAMP group, the seventh group was a *L. plantarum* FCQHC24L1/pMG36e-Usp45-Linker-CRAMP group, and the eighth group was a *L. plantarum* FCQHC24L1/pNZ8148-Usp45-Linker-CRAMP group. After one week of pre-feeding and feeding with 3% DSS drinking water for 7 days, oral immunization was carried out by gavage with oral vaccines containing the anacultures of different recombinant bacteria for 4 consecutive days at a dose of 160 μL/mouse. Then the mice were sacrificed at day 10, and the changes in the intestinal barrier and flora were determined. The results (in FIGS. 20-26) showed that:

(1) Compared with the 7th day, on the 10th day, the average body weight of mice in each group: increased by 1.084 g in the first group, decreased by 2.85688 g in the second group, decreased by 1.89644 g in the third group, decreased by 1.73336 g in the fourth group, decreased by 0.61004 g in the fifth group, decreased by 0.36816 g in the sixth group, increased by 0.52568 g in the seventh group, and increased by 1.23516 g in the eighth group.

(2) The average colon length of each group on the 10th day was: 9.66 cm in the first group, 5.32 cm in the second group, 6.32 cm in the third group, 6.36 cm in the fourth group, 7.18 cm in the fifth group, 7.44 cm in the sixth group, 8.2 cm in the seventh group, and 8.32 cm in the eighth group.

(3) The DAI score results of each group on the 10th day were: 0.2 in the first group, 7.2 in the second group, 6.6 in the third group, 6.0 in the fourth group, 4.6 in the fifth group, 4.8 in the sixth group, 3.6 in the seventh group, and 3.6 in the eighth group.

(4) The score results of colon morphology of each group were: 0.2 in the first group, 3.8 in the second group, 3.2 in the third group, 3.2 in the fourth group, 2.6 in the fifth group, 2.6 in the sixth group, 2.0 in the seventh group, and 2.0 in the eighth group.

(5) The changes in colonic tight junction proteins of each group were: compared with the first group, the expression levels of ZO-1 ($p<0.01$), ZO-2 ($p<0.0001$) and occludin ($p<0.0001$) of the second group were significantly decreased; compared with the second group, the expression levels of ZO-1 ($p<0.05$) and occludin ($p<0.05$) of the fifth and sixth groups were significantly increased, and there was no significant difference in ZO-2; and compared with the second group, the expression levels of ZO-1 ($p<0.01$), ZO-2 ($p<0.01$) and occludin ($p<0.05$) of the seventh and eighth groups were significantly increased.

(6) The changes in colonic inflammatory cytokines of each group were: compared with the first group, IL-6 ($p<0.0001$), IL-1β ($p<0.0001$), and TNF-α ($p<0.0001$) of the second group were significantly increased, and IL-10 ($p<0.0001$) was significantly decreased; and compared with the second group, IL-6 ($p<0.05$), IL-1β ($p<0.05$), and TNF-α ($p<0.05$) of the fifth to eighth groups were significantly decreased, and IL-10 ($p<0.05$) was significantly increased.

(7) The changes in protein levels of key colonic transcription factors in each group were: compared with the first group, p-ERK/ERK ($p<0.0001$), p-p38/p38 ($p<0.0001$) and p-NF-κB/NF-κB ($p<0.0001$) of the second group were significantly increased; compared with the second group, p-ERK/ERK ($p<0.05$) of the fifth group were significantly decreased, and there was no significant difference in p-p38/p38 ($p>0.05$) and p-NF-κB/NF-κB ($p>0.05$); compared with the second group, p-ERK/ERK ($p<0.01$), p-p38/p38 ($p<0.05$) and p-NF-κB/NF-κB ($p<0.05$) of the sixth group were significantly decreased; and compared with the second group, p-ERK/ERK($p<0.01$), p-p38/p38($p<0.05$) and p-NF-κB/NF-κB($p<0.05$) of the seventh and eighth groups were significantly decreased.

(8) Colonic CRAMP protein expression of each group: Compared with the first group, CRAMP protein expression of the second group was significantly decreased ($p<0.0001$); and compared with the second group, CRAMP protein expression of the fifth to eighth groups was significantly increased ($p<0.05$).

The above results show that the fifth group with oral administration of the anaculture of the recombinant strain *L. plantarum* FCQHC24L1/pMG36e-CRAMP, the sixth group with oral administration of the anaculture of the recombinant strain *L. plantarum* FCQHC24L1/pNZ8148-CRAMP, the seventh group with oral administration of the anaculture of the recombinant strain *L. plantarum* FCQHC24L1/pNZ8148-Usp45-Linker-CRAMP, and the eighth group with oral administration of the anaculture of the recombinant strain *L. plantarum* FCQHC24L1/pMG36e-Usp45-Linker- CRAMP all have good effects of restoring the body weight of mice with colitis, restoring the length of the colon, reducing inflammation in the colon, inhibiting secretion of inflammatory cytokines, inhibiting activation of inflammatory signaling pathways, restoring the intestinal barrier, and thereby treating colitis. Moreover, the seventh *L. plantarum* FCQHC24L1/pNZ8148-Usp45-Linker-CRAMP group and the eighth *L. plantarum* FCQHC24L1/pMG36e-Usp45-Linker-CRAMP group have better treatment effects.

The inventor also tried to combine *L. plantarum* with nisin. For example, after mice were subjected to gavage with the *L. plantarum* FCQHC24L1/pNZ8148-CRAMP or the *L. plantarum* FCQHC24L1/pNZ8148-Usp45-Linker-CRAMP for a period of time to make the *L. plantarum* FCQHC24L1/pNZ8148-CRAMP or the *L. plantarum* FCQHC24L1/pNZ8148-Usp45-Linker-CRAMP colonize in the intestinal tract, the treated subjects were administered with nisin or a product with a nisin content, thereby achieving the effect of timed and directional release of CRAMP in the intestinal tract.

Comparative Example 2 Construction of secretory recombinant *L. plantarum* Containing CRAMP Gene Taking secretory recombinant *L. lactis* containing the CRAMP gene in the prior art as a control, the CRAMP gene (GGACTTCTCCGCAAAGGTGGGGAGAAGATTGGTGAAAAGCTTAAGAAAATTGG CCAGAAAATTAAGAATTTTTTTCAGAAACTTGTACCTCAGCCAGAG, SEQ ID NO: 14) expressed thereof was not codon-optimized, there was no Usp45 signal peptide to promote extracellular secretion of CRAMP, intracellular self-cleavage of the Usp45 signal peptide and CRAMP gene cannot be promoted, the content of CRAMP protein secreted in supernatant was low, and the expression product was about 1.5 ng/μL.

Figure 18:
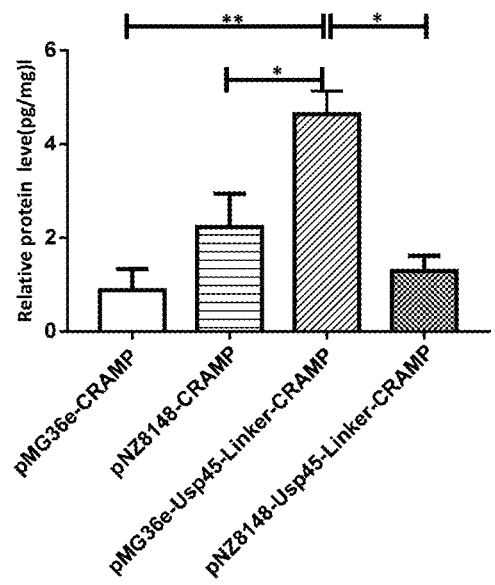
FIG. 18 is the ELISA results of recombinant CRAMP-encoding L. plantarum.
Figure 19:
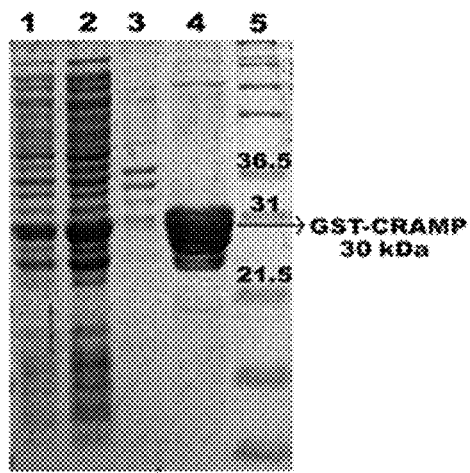
FIG. 19 is the expression of CRAMP in E. coli in the prior art; 1 is the expression of CRAMP in an E. coli lysate; 2 is the expression of CRAMP in the supernatant of the E. coli lysate; 3 is the expression of CRAMP in the precipitation of the E. coli lysate; 4 is the expression of CRAMP in a GST-CRAMP elution buffer on an elution column; and 5 is the protein Marker.
Figure 20:
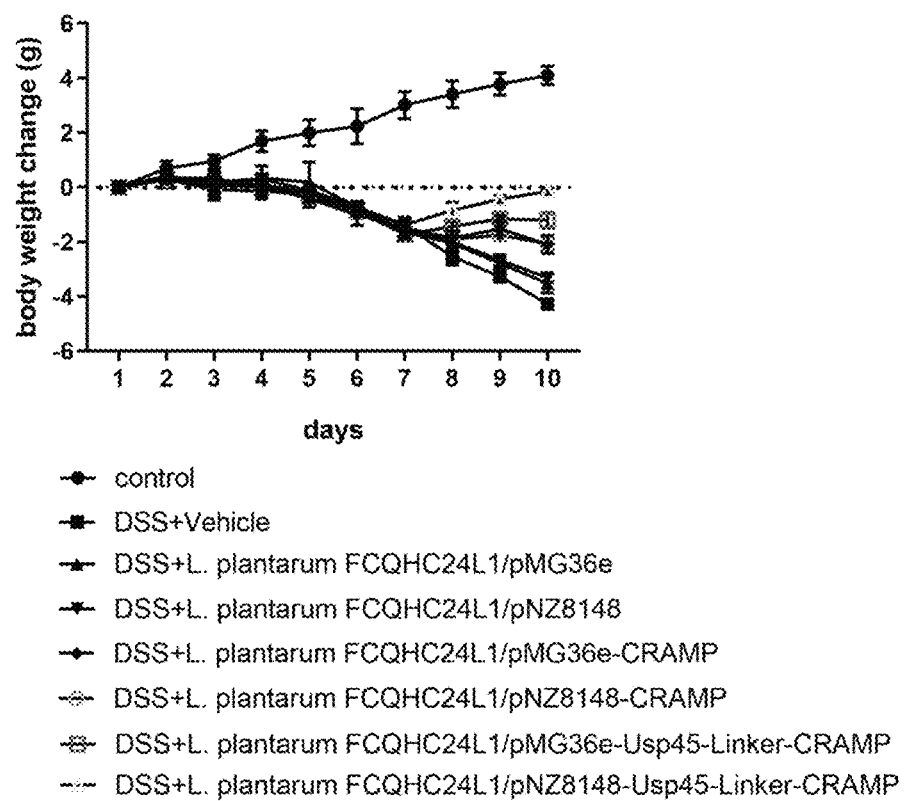
FIG. 20 is changes in the body weight of mice in each group during the construction of colitis animal models.
Figure 21A:
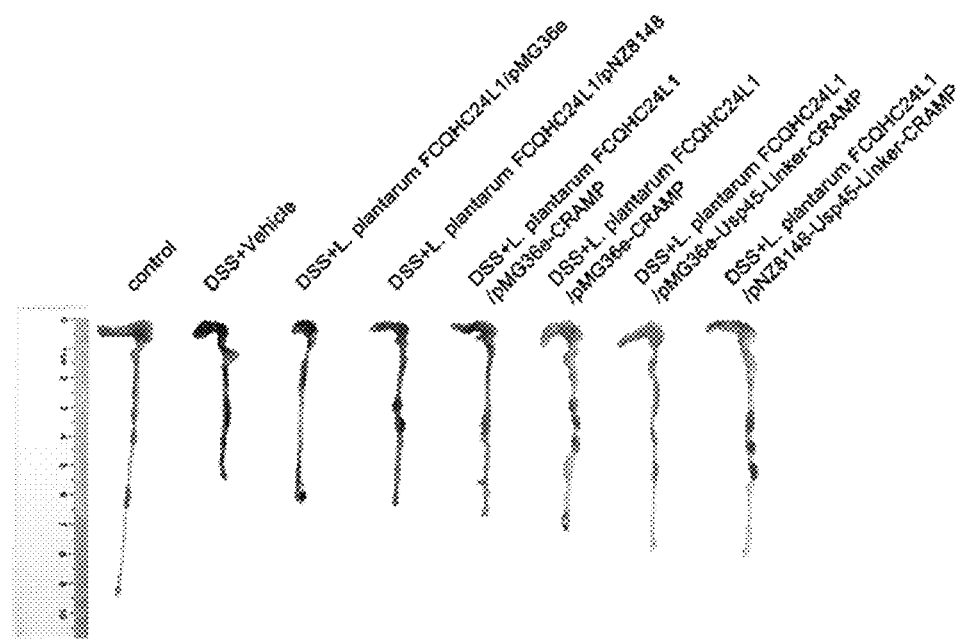
FIG. 21A is a comparison of the colon length of mice in each group.
Figure 21B:
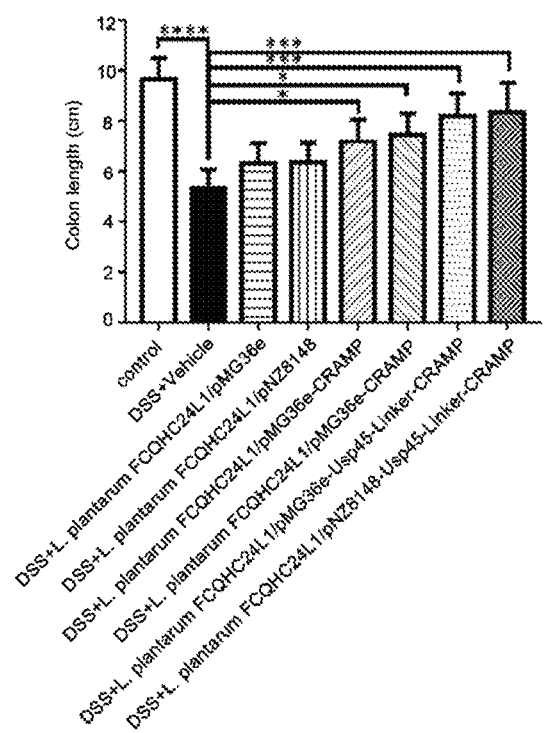
FIG. 21B is a statistical diagram of the colon length of mice in each group.
Figure 22:
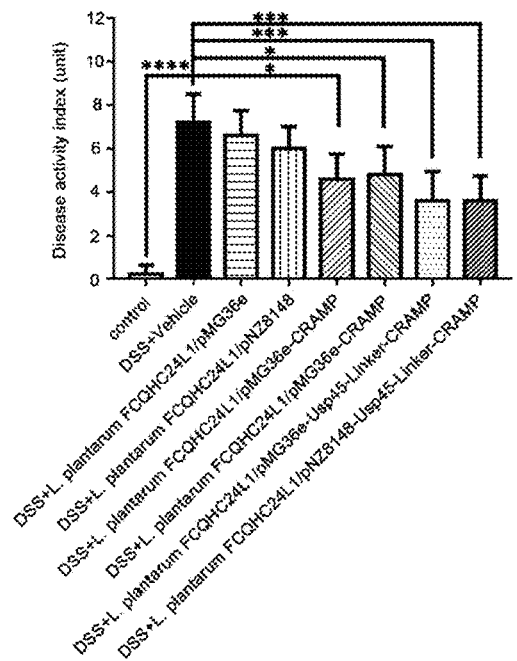
FIG. 22 is the scores of clinical indicators of colitis.
Figure 23A:
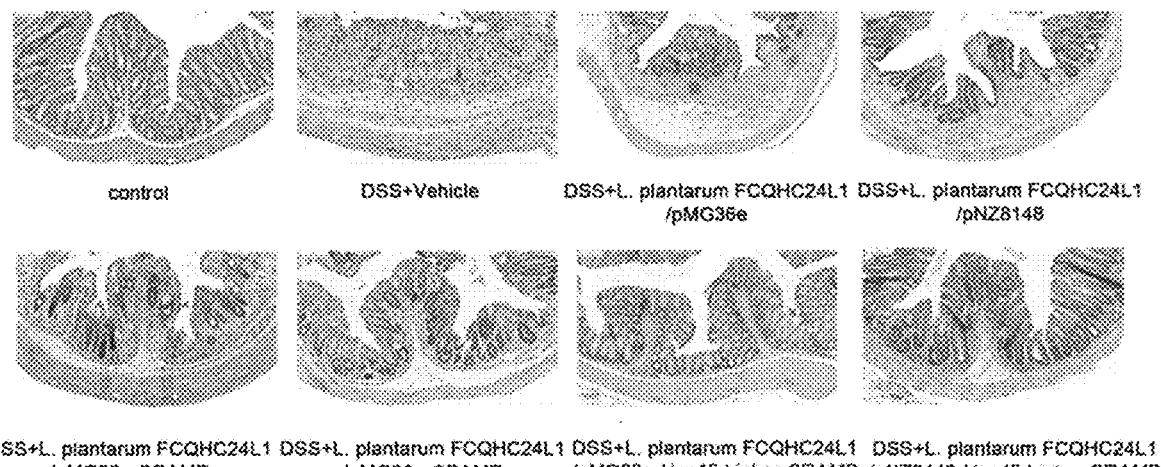
FIG. 23A is an observation diagram of the histopathological morphology of the colon.
Figure 23B:
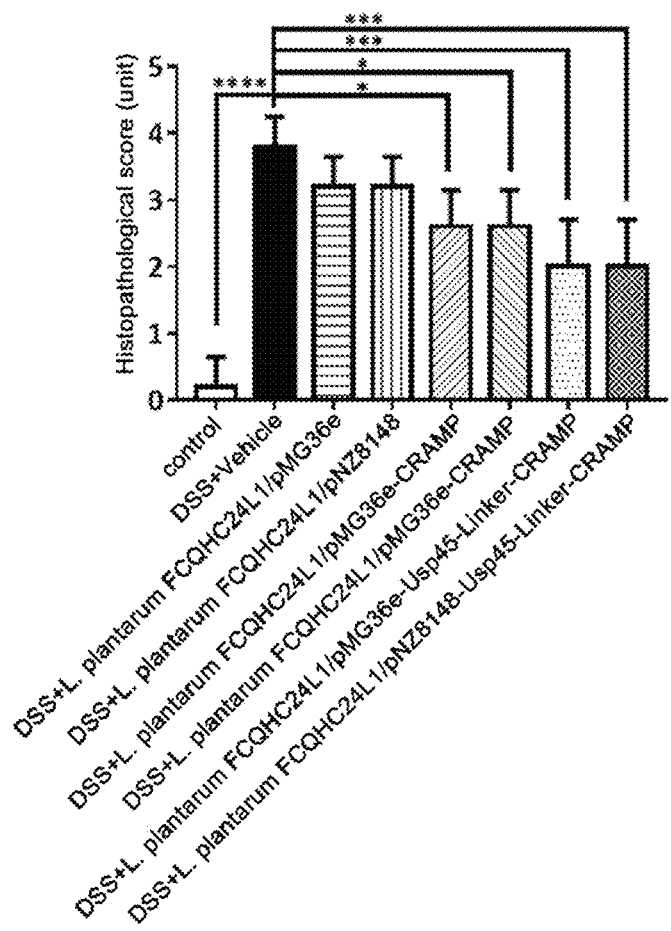
FIG. 23B is histopathological scoring.
Figure 24A:
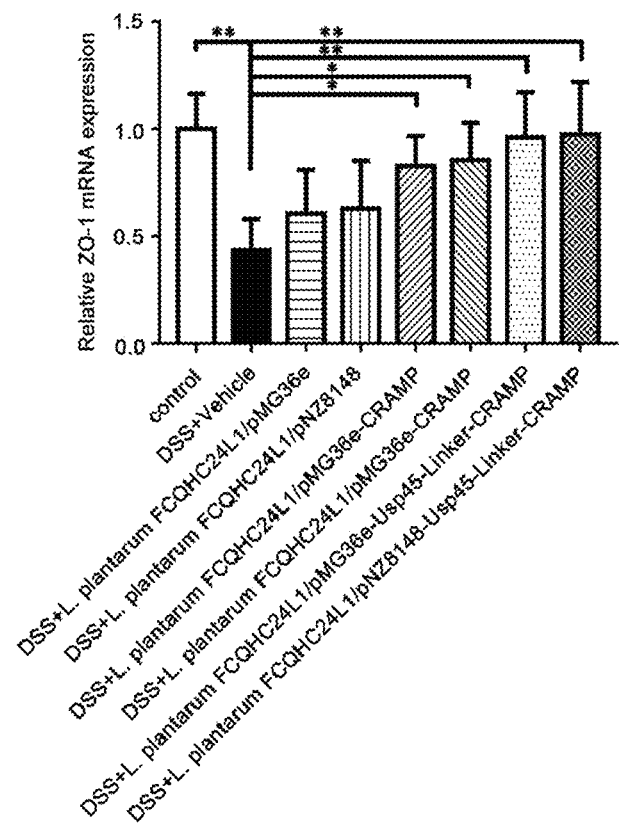
FIG. 24A is changes in an intestinal tight junction protein ZO-1 measured by qPCR.
Figure 24B:
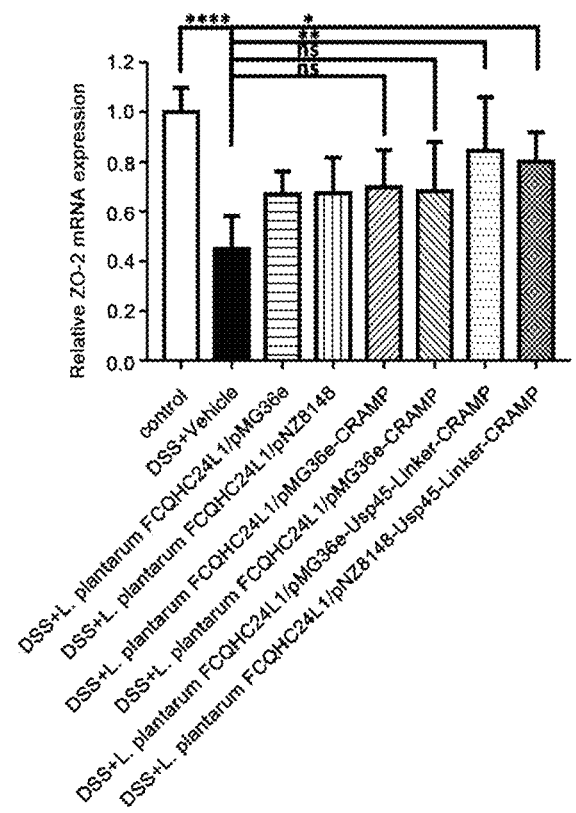
FIG. 24B is changes in an intestinal tight junction protein ZO-2 measured by qPCR.
Figure 24C:
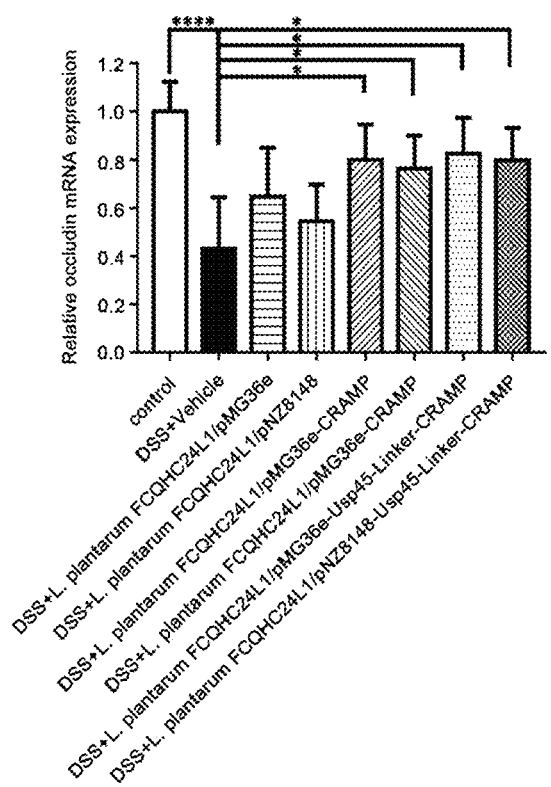
FIG. 24C is changes in an intestinal tight junction protein occludin measured by qPCR.
Figure 25A:
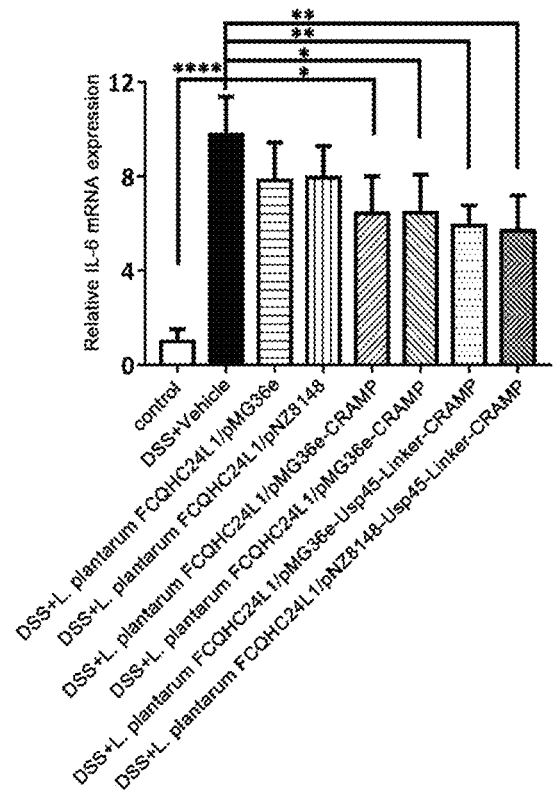
FIG. 25A is the expression of inflammatory cytokine IL-6 measured by qPCR.
Figure 25B:
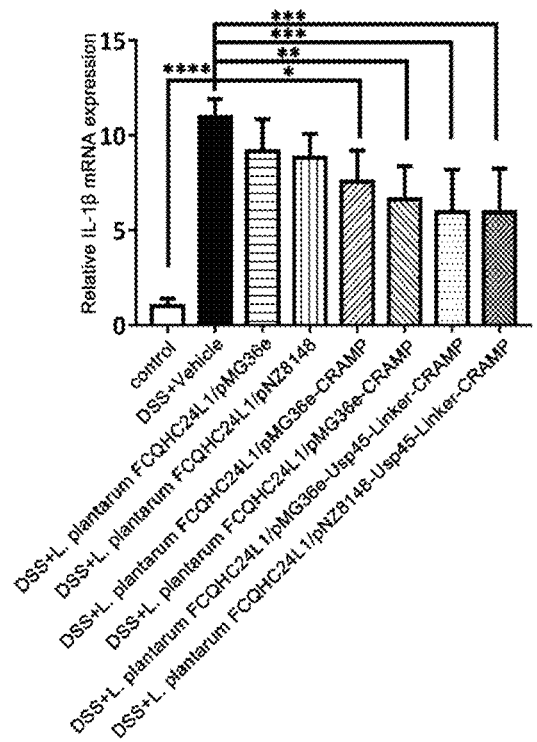
FIG. 25B is the expression of inflammatory cytokine IL-1β measured by qPCR.
Figure 25C:
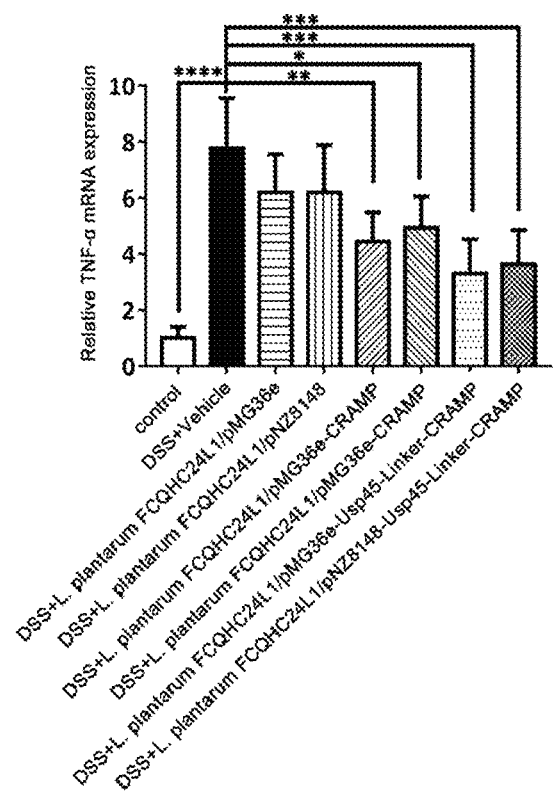
FIG. 25C is the expression of inflammatory cytokine TNF-α measured by qPCR.
Figure 25D:
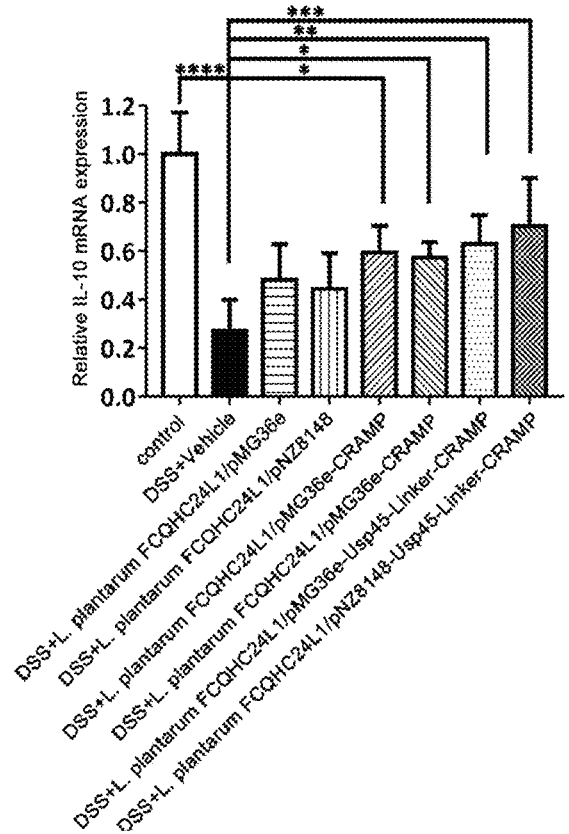
FIG. 25D is the expression of anti-inflammatory cytokine IL-10 measured by qPCR.
Figure 26A:
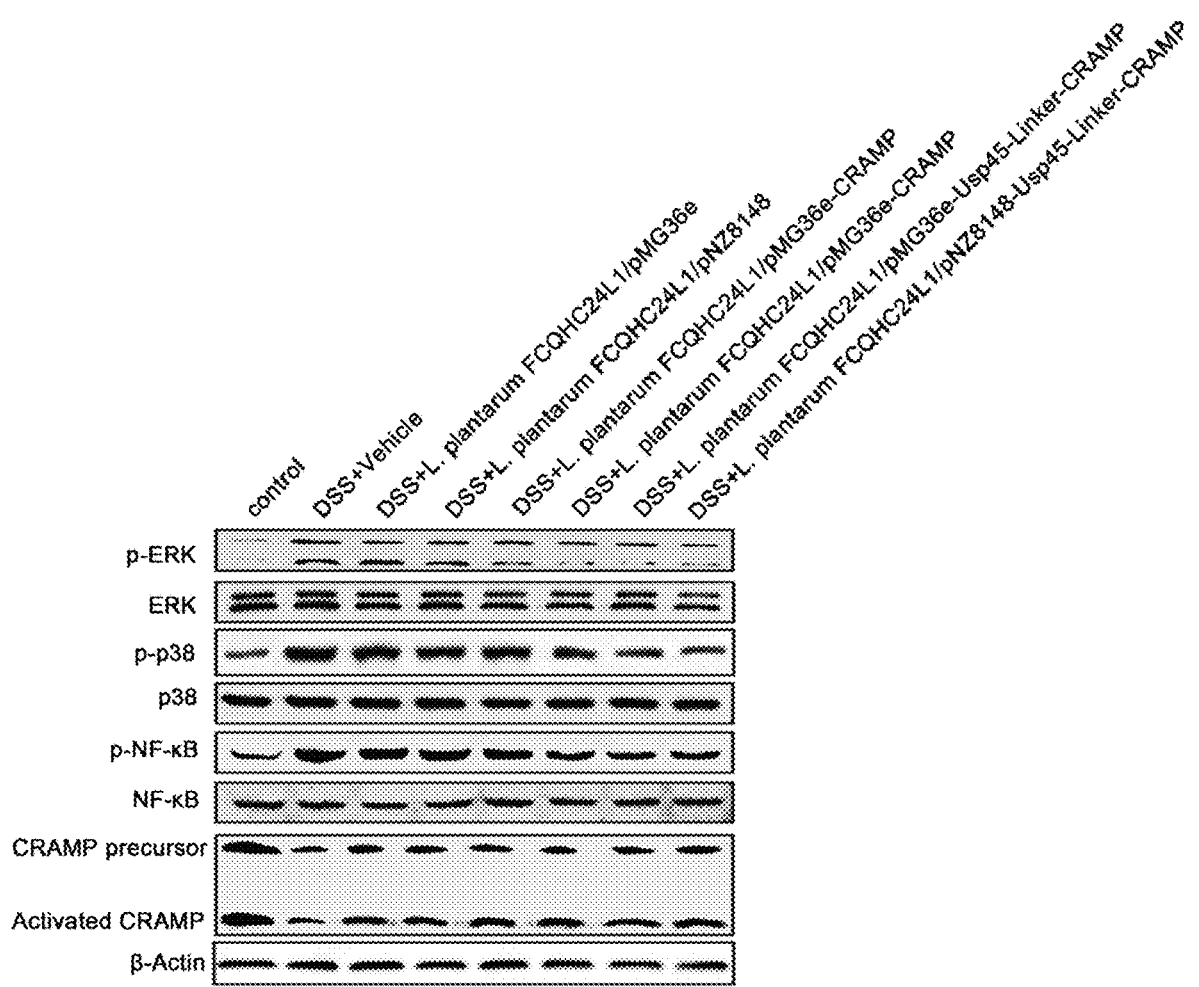
FIG. 26A is changes in phosphorylation levels of inflammation signaling pathway key transcription factors p-EPK, EPK, p-p38, p38, p-NF-κB and NF-κB measured by Western blot.
Figure 26B:
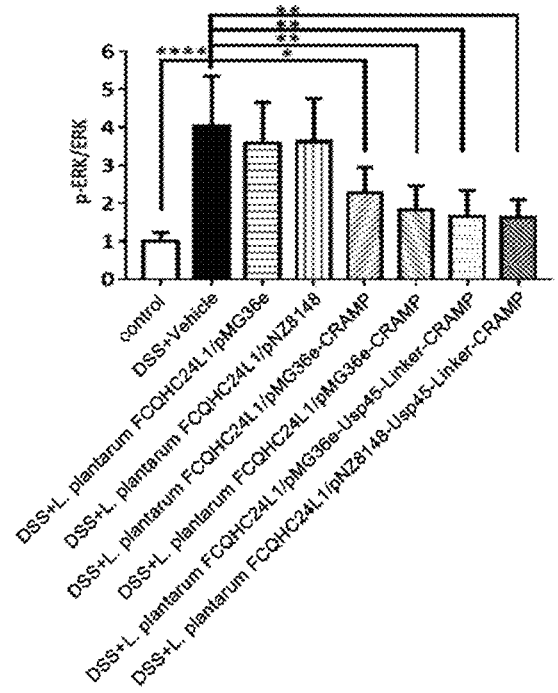
FIG. 26B is changes in the phosphorylation levels of the inflammation signaling pathway key transcription factors p-ERK/ERK measured by Western blot.
Figure 26C:
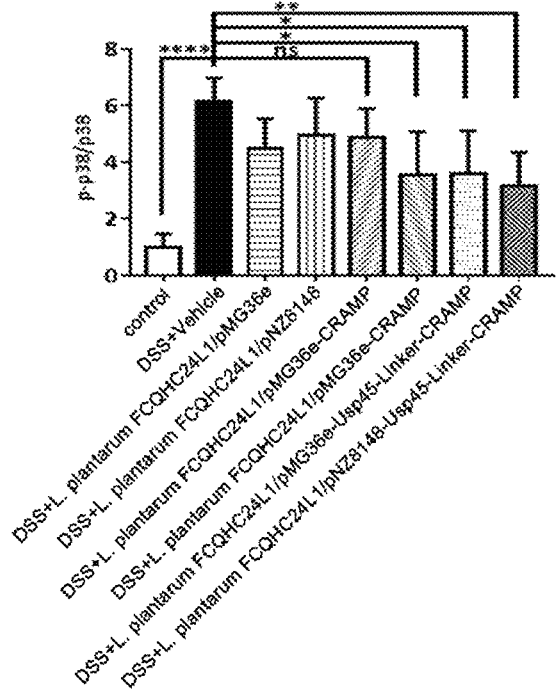
FIG. 26C is changes in the phosphorylation levels of the inflammation signaling pathway key transcription factors p-p38/p38 measured by Western blot.
Figure 26D:
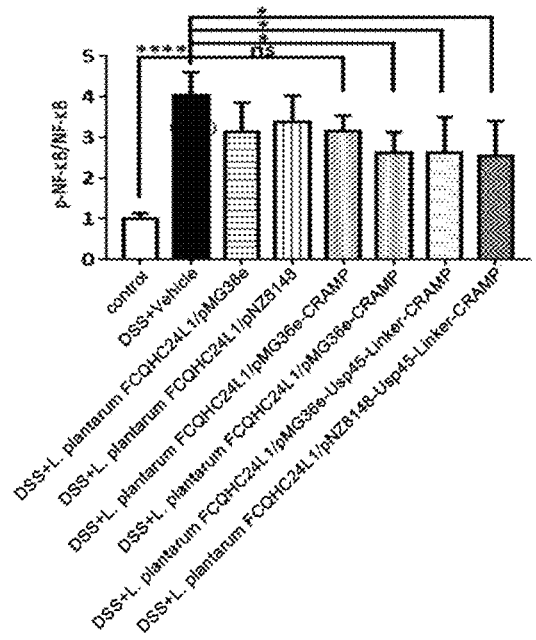
FIG. 26D is changes in the phosphorylation levels of the inflammation signaling pathway key transcription factors p-NF-κB/NF-κB measured by Western blot.
Figure 26E:
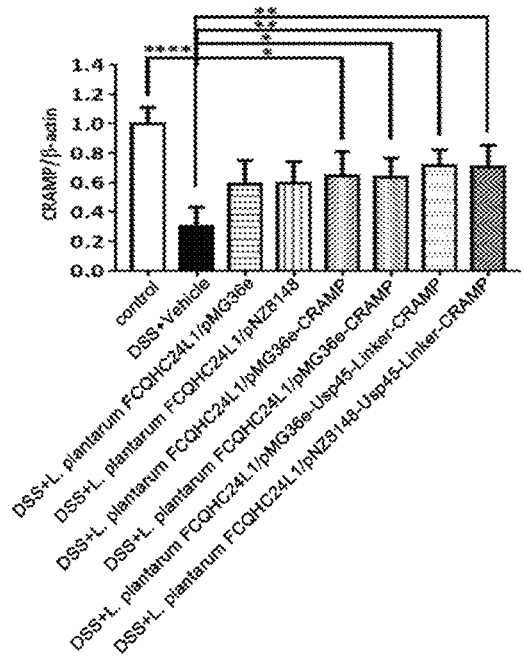
FIG. 26E is expression levels of CRAMP/β-actin measured by Western blot.

The ability of the recombinant strain constructed in Example 11 to express CRAMP was compared with that of the recombinant strain of Comparative Example 1. According to ELISA (FIG. 18), the expression levels of extracellular CRAMP proteins of the recombinant *L. plantarum* FCQHC24L1/pMG36e-CRAMP and the *L. plantarum* FCQHC24L1/pNZ8148-CRAMP without Usp45-induced secretion were about 10 ng/μL, which was 6-8 times higher than that of the extracellular protein secretion of the recombinant strain in Comparative Example 1; the expression level of CRAMP protein of the recombinant *L. plantarum* FCQHC24L1/pNZ8148-Usp45-Linker-CRAMP was about 20 ng/μL, which was 13 times higher than that of Comparative Example 1 (1.5 ng/4); and the level of extracellular CRAMP protein secreted by the recombinant *L. plantarum* FCQHC24L1/pMG36e-Usp45-Linker-CRAMP was higher than 50 ng/μL, which was 30 times higher than the expression level (1.5 ng/μL) in Comparative Example 1 under same conditions.

Although the disclosure has been disclosed as above in preferred examples, it is not intended to limit the disclosure. Anyone skilled in the art can make various changes and modifications without departing from the spirit and scope of the disclosure. Therefore, the protection scope of the disclosure should be defined by the claims.

---

What is claimed is:

1. An isolated gene encoding a cathelicidin-related antimicrobial peptide (CRAMP), wherein the nucleotide sequence of the gene is set forth in SEQ ID NO: 1.

2. A vector comprising the gene of claim 1.

3. The vector of claim 2, wherein the vector is pMG36e or pNZ8148.

4. A recombinant *Lactobacillus* or a recombinant *Lactococcus* expressing the gene of claim 1, wherein the gene is set forth in SEQ ID NO: 1.

5. The recombinant *Lactobacillus* or the recombinant *Lactococcus* of claim 4, wherein the recombinant *Lactobacillus* is *Lactobacillus plantarum* or the recombinant *Lactococcus* is *Lactococcus lactis*.

6. The recombinant *Lactobacillus* of claim 4, wherein the *Lactobacillus* comprises a Usp45 signal peptide to promote expression of the CRAMP.

7. The recombinant *Lactobacillus* of claim 4, wherein the Usp45 signal peptide is linked to the CRAMP through a linker.

8. The *Lactobacillus* of claim 7, wherein the linker comprises two or more amino acid residues selected from Gly and Ser.

9. An edible or medicinal composition comprising the recombinant *Lactobacillus* or the recombinant *Lactococcus* of claim 4.

10. An edible or medicinal composition comprising the recombinant *Lactobacillus* or the recombinant *Lactococcus* of claim 4.

11. The composition of claim 10, wherein the concentration of the recombinant *Lactobacillus* or the recombinant *Lactococcus* is greater than or equal to $1\times10^5$ CFU/mL or $1\times10^5$ CFU/g.

12. An oral vaccine comprising the recombinant *Lactobacillus* or the recombinant *Lactococcus* of claim 4 or a pure culture of the recombinant *Lactobacillus* or the recombinant *Lactococcus*.

* * * * *

SEQUENCE LISTING

```
<160> NUMBER OF SEQ ID NOS: 14

<210> SEQ ID NO 1
<211> LENGTH: 102
<212> TYPE: DNA
<213> ORGANISM: Artificial sequence
<220> FEATURE:
<223> OTHER INFORMATION: Synthetic DNA

<400> SEQUENCE: 1
ggtctgctgc gtaaaggcgg cgagaagatc ggcgagaagc tgaagaagat cggccagaag      60
atcaagaact tcttccagaa actggtgccg cagccggaat aa                        102

<210> SEQ ID NO 2
<211> LENGTH: 34
<212> TYPE: PRT
<213> ORGANISM: Artificial sequence
<220> FEATURE:
<223> OTHER INFORMATION: Synthetic DNA

<400> SEQUENCE: 2

Gly Leu Leu Arg Lys Gly Gly Glu Lys Ile Gly Glu Lys Leu Lys Lys
1               5                   10                  15

Ile Gly Gln Lys Ile Lys Asn Phe Phe Gln Lys Leu Val Pro Gln Pro
            20                  25                  30

Glu Gln

<210> SEQ ID NO 3
<211> LENGTH: 114
<212> TYPE: DNA
<213> ORGANISM: Artificial sequence
<220> FEATURE:
<223> OTHER INFORMATION: Synthetic DNA
```

<400> SEQUENCE: 3

```
atgaaaaaaa aaatcatcag cgcgattctg atgagcaccg ttattctgag tgccgccgcc    60
ccactgagtg gcgtttatgc cgacaccaac agcgatatcg ccaaacaaga tgcc          114
```

<210> SEQ ID NO 4
<211> LENGTH: 228
<212> TYPE: DNA
<213> ORGANISM: Artificial sequence
<220> FEATURE:
<223> OTHER INFORMATION: Synthetic DNA

<400> SEQUENCE: 4

```
gcatgcatga aaaaaaaaat catcagcgcg attctgatga gcaccgttat tctgagtgcc    60
gccgccccac tgagtggcgt ttatgccgac accaacagcg atatcgccaa acaagatgcc   120
ggtctgctgc gtaaaggcgg cgagaagatc ggcgagaagc tgaagaagat cggccagaag   180
atcaagaact tcttccagaa actggtgccg cagccggaat aatctaga                228
```

<210> SEQ ID NO 5
<211> LENGTH: 40
<212> TYPE: DNA
<213> ORGANISM: Artificial sequence
<220> FEATURE:
<223> OTHER INFORMATION: Synthetic DNA

<400> SEQUENCE: 5

```
tctagaatga aaaaaaaaat catcagcgcg attctgatga                          40
```

<210> SEQ ID NO 6
<211> LENGTH: 40
<212> TYPE: DNA
<213> ORGANISM: Artificial sequence
<220> FEATURE:
<223> OTHER INFORMATION: Synthetic DNA

<400> SEQUENCE: 6

```
gcatgcttat tccggctgcg gcaccagttt ctggaagaag                          40
```

<210> SEQ ID NO 7
<211> LENGTH: 40
<212> TYPE: DNA
<213> ORGANISM: Artificial sequence
<220> FEATURE:
<223> OTHER INFORMATION: Synthetic DNA

<400> SEQUENCE: 7

```
gcatgcatga aaaaaaaaat catcagcgcg attctgatga                          40
```

<210> SEQ ID NO 8
<211> LENGTH: 40
<212> TYPE: DNA
<213> ORGANISM: Artificial sequence
<220> FEATURE:
<223> OTHER INFORMATION: Synthetic DNA

<400> SEQUENCE: 8

```
tctagattat tccggctgcg gcaccagttt ctggaagaag                          40
```

<210> SEQ ID NO 9
<211> LENGTH: 15
<212> TYPE: DNA
<213> ORGANISM: Artificial sequence
<220> FEATURE:

<223> OTHER INFORMATION: Synthetic DNA

<400> SEQUENCE: 9
ggcggtggcg gcagc                                                          15

<210> SEQ ID NO 10
<211> LENGTH: 243
<212> TYPE: DNA
<213> ORGANISM: Artificial sequence
<220> FEATURE:
<223> OTHER INFORMATION: Synthetic DNA

<400> SEQUENCE: 10
gcatgcatga aaaaaaaat catcagcgcg attctgatga gcaccgttat tctgagtgcc         60
gccgccccac tgagtggcgt ttatgccgac accaacagcg atatcgccaa acaagatgcc        120
ggtggtggtg gtagcggtct gctgcgtaaa ggcggcgaga agatcggcga agctgaag          180 aagatcggcc agaagatcaa gaacttcttc agaaactgg tgccgcagcc ggaataatct         240
aga                                                                      243

<210> SEQ ID NO 11
<211> LENGTH: 33
<212> TYPE: DNA
<213> ORGANISM: Artificial sequence
<220> FEATURE:
<223> OTHER INFORMATION: Synthetic DNA

<400> SEQUENCE: 11
tctagaggtc tgctgcgtaa aggcggcgag aag                                      33

<210> SEQ ID NO 12
<211> LENGTH: 33
<212> TYPE: DNA
<213> ORGANISM: Artificial sequence
<220> FEATURE:
<223> OTHER INFORMATION: Synthetic DNA

<400> SEQUENCE: 12
gcatgcggtc tgctgcgtaa aggcggcgag aag                                      33

<210> SEQ ID NO 13
<211> LENGTH: 5
<212> TYPE: PRT
<213> ORGANISM: Artificial sequence
<220> FEATURE:
<223> OTHER INFORMATION: protein translated from synthetic DNA

<400> SEQUENCE: 13

Gly Gly Gly Gly Ser
1               5

<210> SEQ ID NO 14
<211> LENGTH: 99
<212> TYPE: DNA
<213> ORGANISM: Artificial sequence
<220> FEATURE:
<223> OTHER INFORMATION: Synthetic DNA

<400> SEQUENCE: 14
ggacttctcc gcaaaggtgg ggagaagatt ggtgaaaagc ttaagaaaat tggccagaaa         60
attaagaatt tttttcagaa acttgtacct cagccagag                                99